US008653642B2

(12) United States Patent
Sutanto et al.

(10) Patent No.: US 8,653,642 B2
(45) Date of Patent: Feb. 18, 2014

(54) METHOD FOR CREATING AND PACKAGING THREE DIMENSIONAL STACKS OF BIOCHIPS CONTAINING MICROELECTRO-MECHANICAL SYSTEMS

(71) Applicant: Arizona Board of Regents, a body corporate for the State of Arizona acting for and on behalf of Arizona, Scottsdale, AZ (US)

(72) Inventors: Jemmy Sutanto, Scottsdale, AZ (US); Jitendran Muthuswamy, Chandler, AZ (US)

(73) Assignee: Arizona Board of Regents, a body corporate of the State of Arizona, acting for and on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 13/711,118

(22) Filed: Dec. 11, 2012

(65) Prior Publication Data

US 2013/0134604 A1    May 30, 2013

Related U.S. Application Data

(63) Continuation of application No. PCT/US2011/040965, filed on Jun. 17, 2011.

(60) Provisional application No. 61/356,515, filed on Jun. 18, 2010.

(51) Int. Cl.
*H01L 23/02* (2006.01)

(52) U.S. Cl.
USPC .............. 257/686; 257/777; 257/E25.006; 257/E25.013; 257/E25.021; 257/E25.027; 257/E23.085; 438/109

(58) Field of Classification Search
USPC .............. 257/777, 686, E25.006, E25.013, 257/E25.021, E25.027, E23.085; 438/109, 438/FOR. 368, FOR. 426
See application file for complete search history.

(56) References Cited

U.S. PATENT DOCUMENTS

| | | | |
|---|---|---|---|
| 6,621,155 B1 * | 9/2003 | Perino et al. | 257/686 |
| 6,759,309 B2 | 7/2004 | Gross | |
| 7,619,305 B2 * | 11/2009 | Fan et al. | 257/686 |
| 2009/0218668 A1 | 9/2009 | Zhe et al. | |
| 2010/0072626 A1 | 3/2010 | Theuss et al. | |
| 2010/0190294 A1 | 7/2010 | Simmons-Matthews | |

OTHER PUBLICATIONS

International Search Report and Written Opinion PCT/US2011/04096 dated Oct. 14, 2011.
International Preliminary Report on Patentability, PCT/US2011/040965 dated Dec. 19, 2012.
Witvrouw, CMOS-MEMS Integration: Why, How and What?. 2006, ICCAD '06 Proceedings of the 2006 IEEE/ACM international conference on Computer-aided design, pp. 826-827.
Chen et al., A novel plastic package for pressure sensors fabricated using the lithographic dam-ring approach. 2009, Sensors and Actuators A, vol. 149, pp. 165-171.

(Continued)

*Primary Examiner* — Jasmine Clark
(74) *Attorney, Agent, or Firm* — Snell & Wilmer L.L.P.

(57) ABSTRACT

Systems and methods of the present disclosure provide for three-dimensional stacks of microelectromechanical (MEMS) systems, such as sensors. The stacks may be encapsulated and sealed, and can be positioned within biological tissue, for example to monitor biological signals within the volume of the sensor, provide stimulating signals to a brain, and so forth.

13 Claims, 32 Drawing Sheets

(56) References Cited

OTHER PUBLICATIONS

Pai et al., The viability of anisotropic conductive film as a flip chip interconnect technology for MEMS devices. 2005, J Micromech Microeng, vol. 15, pp. 1131-1139.

Candler et al., Single Wafer Encapsulation of MEMS Devices. 2003, IEEE Transactions on Advanced Packaging, vol. 26, pp. 227-232.

Ayanoor et al., Development of wafer scale encapsulation process for large displacement piezoresistive MEMS devices. 2009, Sensors and Actuators A, vol. 156, pp. 275-283.

Graham et al., A Method for Wafer-Scale Encapsulation of Large Lateral Deflection MEMS Devices. 2010, Journal of Microelectromechanical Systems, vol. 19, pp. 28-37.

Jackson et al., Nonhermetic Encapsulation Materials for MEMS-Based Movable Microelectrodes for Long-Term Implantation in the Brain. 2009, Journal of Microelectromechanical Systems, vol. 18, pp. 1234-1245.

O'Mahony et al., Wafer-level thin-film encapsulation for MEMS. 2009, Microelectronic Engineering, vol. 86, pp. 1311-1313.

Leroy et al., High Quality Factor Copper Inductors on Wafer-Level Quartz Package for RF MEMS Applications. 2006, Proceedings of the Solid-State Device Research Conference, pp. 190-193.

Ding et al., A Wafer-level Protective Technique Using Glass Caps for MEMS Gyroscopes. 2006, Solid-State and Integrated Circuit Technology, 8th International Conference on Shanghai, China, pp. 2129-2131.

Joseph et al., Through-silicon vias enable next-generation SiGe power amplifiers for wireless communications. 2008, IBM J Res Dev, vol. 52, pp. 635-648.

Boustedt et al., Flip Chip as an Enabler for MEMS Packaging. 2002, Electronic Components and Technology Conference, pp. 124-128.

Basavanhally et al., High-Density Solder Bump Interconnect for MEMS Hybrid Integration. 2007, IEEE Transactions on Advanced Packaging, vol. 30, pp. 622-628.

Yang et al., 3D Integration of CMOS and MEMS using Mechanically Flexible Interconnects (MFI) and Through Silicon Vias (TSV). 2010, Electronic Components and Technology Conference, pp. 822-828.

Zama et al., Flip Chip Interconnect Systems Using Copper Wire Stud Bump and Lead Free Solder. 2001, IEEE Transactions on Electonics Packaging Manufacturing, vol. 24, pp. 261-268.

Corbin, Finite element analysis for Solder Ball Connect (SBC) structural design optimization. 1993, Ibm J Res Dev, vol. 37, pp. 585-596.

Garrou, Wafer Level Chip Scale Packaging (WL-CSP): an Overview. 2000, IEEE Transactions on Advanced Packaging, vol. 23, pp. 198-205.

Zeng et al., Six cases of reliability study of Pb-free solder joints in electronic packaging technology. 2002, Materials Science and Engineering, vol. 38, pp. 1051-1059.

Zhang et al., An investigation into the effects of flux residues on properties of underfill materials for flip chip packages. 2003, IEEE T Compon Pack T, vol. 26, pp. 233-238.

Reichl et al., Overview and development trends in the field of MEMS packaging. 2001, Micro Electro Mechanical Systems, pp. 1-5.

Chen, Packaging effect investigation of WL-CSP with a central opening: a case study on pressure sensors. 2010, Sensors and Actuators A, vol. 157, pp. 47-53.

Maboudian et al., Self-assembled monolayers as anti-stiction coatings for MEMS: characteristics and recent developments. 2000, Sensors and Actuators, vol. 82, pp. 219-223.

Spengen et al., A physical model to predict stiction in MEMS. 2002, J Micromech Microeng, vol. 12, pp. 702-713.

Cabruja et al., Piezoresistive Accelerometers for MCM-Package—Part II: The Packaging. 2005, J Microelectromech Systems, vol. 14, pp. 806-811.

Campabadal et al., Flip-chip packaging of piezoresistive pressure sensors. 2006, Sensors and Actuators A, vol. 132, pp. 415-419.

Stark et al., A Mold and Transfer Technique for Lead-Free Fluxless Soldering and Application to MEMS Packaging. 2006, J Microelectromech Systems, vol. 15, pp. 849-858.

Plaza et al., Piezoresistive Accelerometers for MCM Package. 2002, J Microelectromech Systems, vol. 11, pp. 794-801.

Miller et al., Microrelay Packaging Technology Using Flip-Chip Assembly. 2000, The 13th Annual International Conference on Micro Electro mechanical systems, pp. 265-270.

Lin et al., Study of Fluxless Soldering Using Formic Acid Vapor. 1999, IEEE Transactions on Advanced Packaging, vol. 22., pp. 592-601.

Heschel et al., Stacking Technology for a Space Constrained Microsystem. 1998, The 11th Annual International Workshop on Micro Electro Mechanical Systems, pp. 312-317.

Singh et al., Batch Transfer of Microstructures using Flip-Chip Solder Bump Bonding. 1997, International Conference on Solid State Sensors and Actuators, pp. 265-268.

Tilmans et al., A Fully-Packaged Electromagnetic Microrelay. 1999, Twelfth IEEE International Conference on Micro Electro Mechanical Systems, pp. 25-30.

Hettak et al., DC-to-50 GHz Compensation Structure for Flip-Chip Assembled SPST MEMS Switch. 2009, IEEE IMS, pp. 597-601.

Oh et al., A New Flip-chip Bonding Technique Using Micromachined Conductive Polymer Bumps. 1999, IEEE Transactions on Advanced Packaging, vol. 22, pp. 586-591.

Oh et al., Flip-Chip Packaging Using Micromachined Conductive Polymer Bumps and Alignment Pedestals for MOEMS. 1999, IEEE Journal of Selected Topics in Quantum Electronics, vol. 5, pp. 119-126.

Li et al., Polymer Flip-chip Bonding of Pressure Sensors on a Flexible Kapton Film for Neonatal Catheters. 2005, J Micromech Microeng, vol. 15, pp. 1729-1735.

Jeon et al., Mechanical Reliability Evaluation of Sn-37Pb Solder Joint Using High Speed Lap-shear Test. 2008, Microelectronic Engineering, vol. 85, pp. 1967-1970.

Ridout et al., Review of Methods to Predict Solder Joint Reliability Under Thermo-mechanical Cycling. 2007, Fatigue Fract Eng M, vol. 30, pp. 400-412.

Irwin et al., Quick Prototyping of Flip Chip Assembly with MEMS. 1998, IEEE, pp. 293-296.

Tuantratnont et al., Bulk-etched Surface Micromachined and Flip-chip Integrated Micromirror Array for Infrared Applications. 2000, IEEE Optical MEMS, pp. 71-72.

Muthuswamy et al., Single Neuronal Recordings Using Surface Micromachined Polysilicon Microelectrodes. 2005, Journal of Neuroscience Methods, vol. 142, pp. 45-54.

Jackson et al., Long-term neural recordings using MEMS based movable microelectrodes in the brain. 2010, Frontiers in Neuroengineering, vol. 3, pp. 1-13.

Jackson et al., Flexible Chip-Scale Package and Interconnect for Implantable MEMS Movable Microelectrodes for the Brain. 2009, Journal of Microelectromechanical Systems, vol. 18.

Indium Inc. (Dec. 15, 2010). Solder Spheres. Available: http://www.indium.com/products/semiconductorpackagingassembly/solderspheres.php.

Vaynman et al., Isothermal Fatigue of Low Tin Lead Based Solder. 1988, Metall Trans A, vol. 19, pp. 1051-1059.

Abgrall et al., A Novel Fabrication Method of Flexible and Monolithic 3D Microfluidic Structures Using Lamination of SU-8 Films. 2006, J Micromech Microeng, vol. 16, pp. 113-121.

Lagally et al., Monolithic Integrated Microfluidic DNA Amplification and Capillary Electrophoresis Analysis System. 2000, Sensor Actuat B-Chem, vol. 63, pp. 138-146.

Goud et al., Electrochemical Biosensors and Microfluidics in Organic System-on-Package Technology. 2007, Electronic Components and Technology Conference, pp. 1550-1555.

Wu et al., Fabrication of complex three-dimensional microchannel systems in PDMS. 2003, J Am Chem Soc, vol. 125, pp. 554-559.

Martinez et al., Three-dimensional microfluidic devices fabricated in layered paper and tape. 2008, Proc Natl Acad Sci USA, vol. 105, pp. 19606-19611.

(56) References Cited

OTHER PUBLICATIONS

Luharuka et al., Simulated and experimental dynamic response characterization of an electromagnetic microvalve. 2008, Sensor Actuat A-Phys, vol. 143, pp. 399-408.

Sutanto et al., Dynamic characteristics of membrane displacement of a bidirectional electromagnetic microactuator with microcoil fabricated on a single wafer. 2005, Microelectron Eng, vol. 82, pp. 12-27.

Gagnard et al., Through silicon via: From the CMOS imager sensor wafer level package to the 3D integration. 2010, Microelectron Eng, vol. 87, pp. 470-476.

Goldberg, How to understand MEMS. 2002, R&D Mag, vol. 44, pp. 37-37.

Sutanto et al., Novel First-Level Interconnect Techniques for Flip-chip on MEMS devices. 2012, J Microelectromechanical Systems, vol. 21., No. 1, pp. 132-144.

* cited by examiner

METHOD FOR CREATING AND PACKAGING THREE DIMENSIONAL STACKS OF BIOCHIPS CONTAINING MICROELECTRO-MECHANICAL SYSTEMS

CROSS REFERENCE TO RELATED APPLICATIONS

This application is a continuation of PCT Application No. US2011/040965 having an international filing date of Jun. 17, 2011 and entitled "METHOD FOR CREATING AND PACKAGING THREE DIMENSIONAL STACKS OF BIOCHIPS CONTAINING MICROELECTRO-MECHANICAL SYSTEMS". PCT Application No. US2011/040965 claims priority to U.S. Provisional Application No. 61/356,515 filed on Jun. 18, 2010 and entitled "METHOD FOR CREATING AND PACKAGING THREE DIMENSIONAL STACKS OF BIOCHIPS CONTAINING MICROELECTRO-MECHANICAL SYSTEMS." The entire contents of all the foregoing applications are hereby incorporated by reference.

FEDERALLY SPONSORED RESEARCH OR DEVELOPMENT

This invention was made with government support under grant number R01NS055312-03-S1 awarded by NIH/NHGRI. The Government has certain rights in the invention.

BACKGROUND

Microelectro-mechanical systems (MEMS) relate to technologies based on an integration of mechanical elements, such as sensors and actuators, and/or electronics that are formed on a common substrate by microfabrication technology. MEMS components range in size from a few microns to a few millimeters. MEMS components are fabricated by microfabrication techniques that include techniques used to fabricate integrated circuits (IC) using IC process sequences (e.g., CMOS, Bipolar, or BICMOS processes). Integrated circuit microfabrication techniques have been used to create three dimensional arrays of electrical components.

Micromechanical components of MEMS systems are fabricated using "micromachining" processes that selectively etch away parts of the silicon wafer or add new structural layers to form the mechanical and electromechanical devices. By combining silicon based microelectronics and micromachining, MEMS technology creates systems and devices in a single chip. MEMS augments the computational ability of microelectronics with the sensing and control functions of microsensors and/or microactuators.

In recent years, advances have been made in the field of neurobiology. An important aspect of further advancement is observation of spatiotemporally distributed neural activity. MEMS technology has been applied to develop a self-anchoring MEMS intrafascicular neural electrode as disclosed by International Publication No. WO 2009/012502 A1, which is expressly incorporated herein by reference.

Several studies using animals have successfully investigated the use of movable microelectrodes that can be precisely positioned in the brain or can be moved in the event of neural-electrode interface failure. However, the size and weight of the movable microelectrodes are often large and interfere with or impair animal movement and/or behavior. Therefore, there is a need for a movable microelectrode device that can be integrated with advanced signal conditioning and control circuitry towards a fully autonomous micro-implant in the brain. There remains a need for apparatus for sensing spatially distributed neural activity and for recording that activity.

BRIEF SUMMARY OF THE INVENTION

An aspect of the invention concerns three dimensional arrays of micro-components including microelectro-mechanical systems (MEMS), micro fluidics and micro-optical components.

Another aspect of the invention concerns a method for fabricating high density three dimensional arrays of micro components.

Yet another aspect of the invention resides in a three dimensional array of sensors that can he positioned within biological tissue to monitor biological signals within the volume of the sensor.

Still another aspect of the invention resides in a three dimensional array of active MEMS devices that provide stimulating signals to a brain.

DETAILED DESCRIPTION OF THE INVENTION

The invention concerns clusters of microelectro-mechanical systems (MEMS) components. In particular, the invention concerns the configuration of a three dimensional stack of MEMS devices and a method of fabricating the stack. A specific application of the invention is a stack of movable microelectrodes that may be positioned within a brain so that the microelectrodes sense electrical impulses of single neurons and neuronal networks and transmit signals created by those electrical impulses for recording.

The present invention is described hereinafter by reference to the accompanying drawings that show embodiments of the invention and in which like numbers refer to like elements throughout. This invention may, however, be embodied in many different forms and should not be construed as limited to the embodiments set forth herein. Rather, these embodiments are examples of the invention, which has the full scope indicated by the claims.

Figure 1:
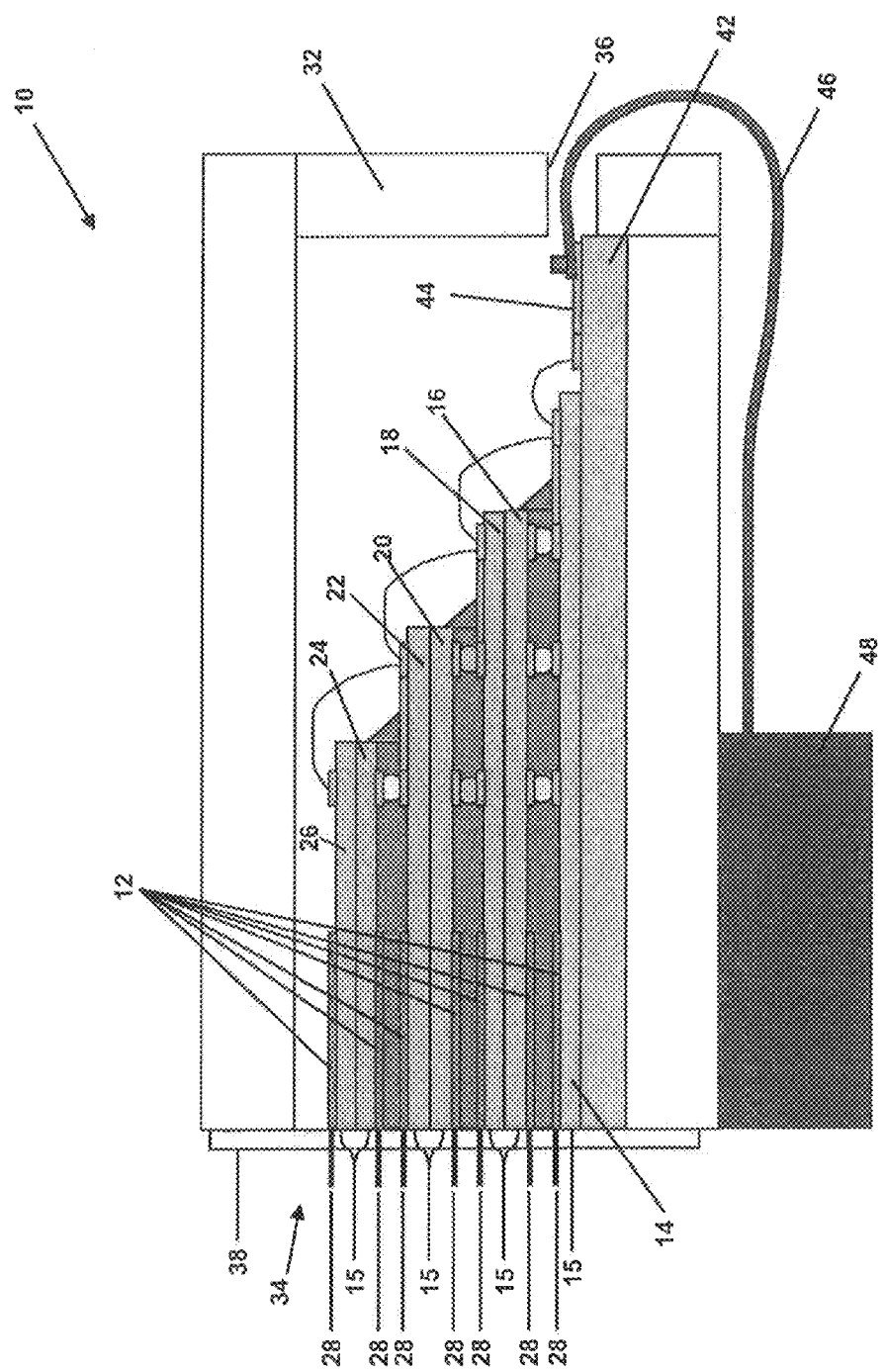
FIG. 1 illustrates a side cross section of a microsensor cluster according to the present invention.

FIG. 1 illustrates a cross section of a microsensor cluster 10 according to the present invention. The cluster 10 includes seven MEMS active microactuators 12. Each microactuator 12 is formed on one of seven silicon substrates 14, 16, 18, 20, 22, 24 and 26. The silicon substrates 14, 16, 18, 20, 22, 24 and 26 each has a thickness that provides sufficient strength to support the microactuator 12 when assembled within the cluster 10 as described herein. The thickness of the silicon substrates may be one half millimeter thick. The substrates 14, 16, 18, 20, 22, 24 and 26 each have a leading edge 15. The substrates 14, 16, 18, 20, 22, 24 and 26 are positioned generally parallel to each other and so that their leading edges 15 lie approximately in a plane.

A microactuator 12 is formed on each substrate 14, 16, 18, 20, 22, 24 and 26. Each microactuator 12 extends on a substrate from the edge 15. A plurality of microelectrodes 28 extend away from each microactuator 12 along the edge 15. The microelectrodes 28 extend generally perpendicular to the edge 15 and generally perpendicular to the plane approximated by the edges 15 of the substrates 14, 16, 18, 20, 22, 24 and 26. The microelectrodes 28 are movably mounted to the microactuators 12. The microactuators 12 are constructed to support and to extend and retract the microelectrodes 28.

The microsensor cluster 10 is positioned within a cover 32. The cover 32 defines an interior and an opening 34. The microcluster 10 is positioned within the interior of the cover 32 so that the edges 15 of the substrates 14, 16, 18, 20, 22, 24 and 26 are at the opening 34. The microelectrodes 28 extend from the microactuators 12 at the opening 34. A non-hermetic mesh encapsulation 38 is secured to the cover 32 to extend over the opening 34. The mesh encapsulation 38 permits the microelectrodes 28 to extend therethrough. Preferably, the mesh is a composite of nylon mesh with silicon gel encapsulation as described by N. Jackson, S. Anand, M. Okandan and J. Muthuswamy, "Non-hermetic Encapsulation Materials for MEMS Based Movable Microelectrodes for Long-Term Implantation in the Brain," IEEE/ASME J Microelectromech Syst, 18(6):1234-1245, 2009.

The microsensor cluster 10 includes a second level interconnect board 42 that is mounted to the cover 32. The second level interconnect board 42 may be made of glass or polyimide and may be one half millimeter thick. The second level interconnect board 42 has connection pads 44 adjacent to the cover 32 at a location that is separated from the opening 34. The connection pads 44 are electrically connected to the microelectrodes 28 and to the microactuators 12 as further described herein. Signals from the microelectrodes 28 are received by the connection pads 44 that are electrically connected to and the microelectrodes 28 and the microactuators 12 are controlled by signals provided to connection pads 44 that electrically connected to the microactuators 12. Conductors 46 are electrically connected to the connection pads 44 and extend through the opening 36 in the cover 32 to an outer connect 48 at which electrical connections to the microelectrodes 28 and the microactuators 12 may be made.

The substrate 14 is mounted to the second level interconnect board 42 as will be described herein. The substrate 16 is mounted to the substrate 14 as will he described herein. The substrate 16 is spaced from the substrate 14 by approximately 60 micrometers. The microactuator 12 mounted to the substrate 14 is positioned on a surface of the substrate 14 that faces the substrate 16. The microactuator 12 mounted to the substrate 16 is positioned on a surface of the substrate 16 that faces the substrate 14. The microactuators 12 mounted to the substrates 14 and 16 are thereby positioned adjacent to and separated from each other within the space separating the substrates 14 and 16.

The substrate 18 overlies and is mounted to the substrate 16 as will be described herein. The substrate 20 is mounted to the substrate 18 as will be described herein. The substrate 20 is spaced from the substrate 18 by approximately 60 micrometers. The microactuator 12 mounted to the substrate 20 is positioned on a surface of the substrate 20 that faces the substrate 18. The microactuator 12 mounted to the substrate 18 is positioned on a surface of the substrate 18 that faces the substrate 20. The microactuators 12 mounted to the substrates 16 and 18 are thereby separated from each other by the substrates 16 and 18 and by the bonding between them. The microactuators 12 mounted to the substrates 18 and 20 are thereby positioned adjacent to and separated from each other within the space separating the substrates 18 and 20.

The substrate 22 overlies and is mounted to the substrate 20 as will be described herein. The substrate 24 is mounted to the substrate 22 as will be described herein. The substrate 24 is spaced from the substrate 22 by 60 micrometers. The microactuator 12 mounted to the substrate 24 is positioned on a surface of the substrate 24 that faces the substrate 22. The microactuator 12 mounted to the substrate 22 is positioned on a surface of the substrate 22 that faces the substrate 24. The microactuators 12 mounted to the substrates 20 and 22 are thereby separated from each other by the substrates 20 and 22 and the bonding between them. The microactuators 12 mounted to the substrates 22 and 24 are thereby positioned adjacent to and separated from each other within the space separating the substrates 22 and 24.

The substrate 26 overlies and is mounted to the substrate 24 as will be described herein. The microactuator 12 mounted to the substrate 26 is positioned on a surface of the substrate 26 that faces away from the substrate 24. The microactuators 12 mounted to the substrates 24 and 26 are thereby separated from each other by the substrates 24 and 26 and by the bonding between them.

Figure 2:
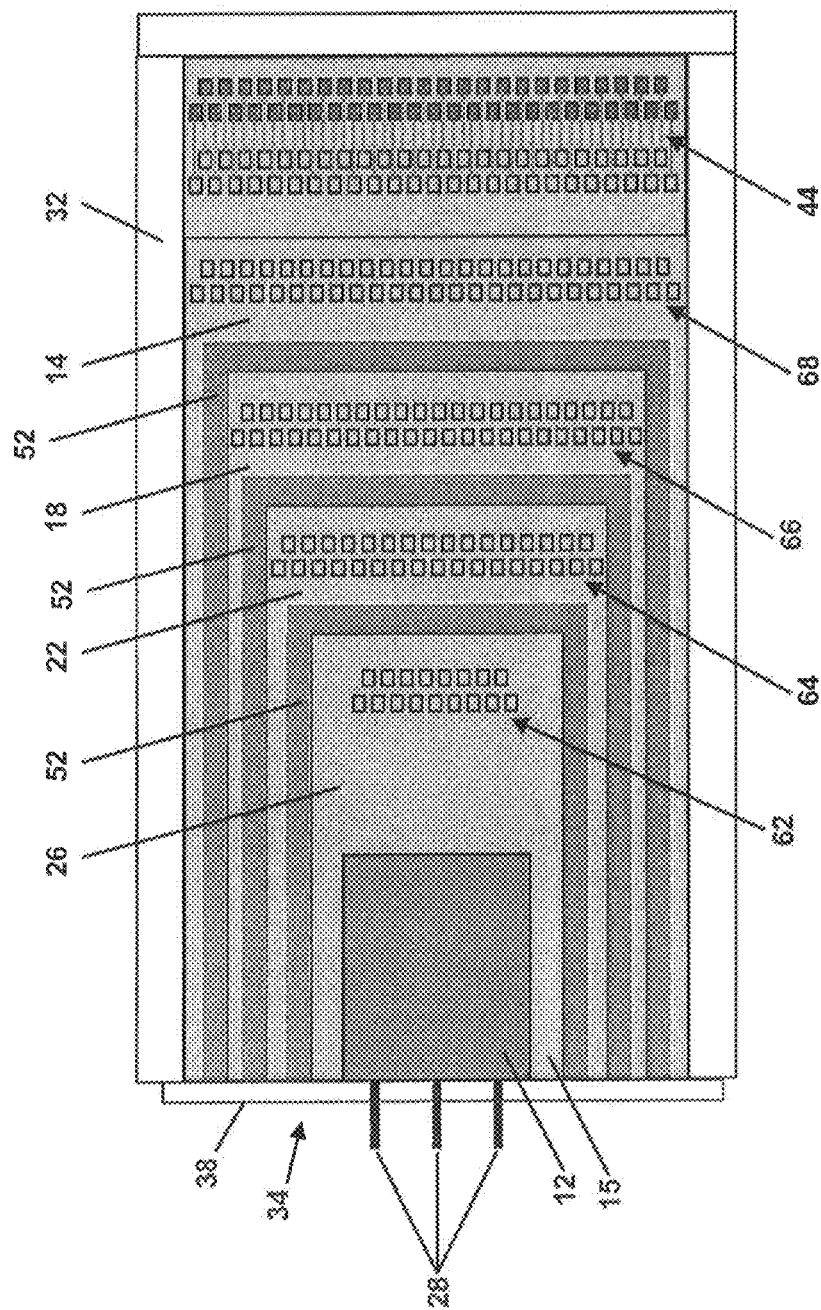
FIG. 2 illustrates a section view of the top of the microsensor cluster as shown by FIG. 1.

FIG. 2 is a view of the microsensor cluster 10 from adjacent to substrate 26. The cover 32 and mesh encapsulation 38 are shown in section. Three microelectrodes 28 are shown extending from the microactuators 12 at separated locations along the edge 15. An underfill material 52 closes and hermetically seals the gap between substrate 24 and substrate 22 around the periphery of the substrate 24 except the periphery that lies along the leading edge 15. Similarly, the underfill material 52 closes and hermetically seals the gap between substrate 20 and substrate 18 around the periphery of the substrate 20 except the periphery that lies along the leading edge 15. The underfill material 52 also closes and hermetically seals the gap between substrate 16 and substrate 14 around the periphery of the substrate 16 except the periphery that lies along the leading edge 15. As presently preferred, the underfill material is a silicon epoxy that is manufactured by DAP Products Inc. The underfill material 52 supports the substrates maintaining the separation between separated substrates.

As shown by FIG. 2, a plurality of connection pads 62 are positioned on an outward facing surface of the substrate 26 that faces oppositely from the substrate 24. These connection pads 62 are electrically connected to the actuator 12 that is on the substrate 26 and the microelectrodes 28 that extend from that actuator 12. Those electrical connections may comprise any electrical connection including conductive paths formed in the substrate 26 by integrated circuit (IC) processes.

A plurality of a plurality of connection pads 64 are positioned on a section of the substrate 22 that extends farther from the leading edge 15 than do substrates 24 and 26. The pads 64 are positioned on a surface of the substrate 22 that faces oppositely from the substrate 20. Connection pads 64 are electrically connected to the actuator 12 that is on the substrate 22 and the microelectrodes 28 that extend from that actuator 12. Others of connection pads 64 are electrically connected to the actuator 12 that is on the substrate 24 and the microelectrodes 28 that extend from that actuator 12. Those electrical connections include connections from the substrate 24 to the substrate 22 as described herein.

A plurality of connection pads 66 are positioned on a section of the substrate 18 that extend farther from the leading edge 15 than do substrates 20 and 22. The pads 66 are positioned on a surface of the substrate 18 that faces oppositely from the substrate 16. Connection pads 66 are electrically connected to the actuator 12 that is on the substrate 18 and the microelectrodes 28 that extend from that actuator 12. Others of connection pads 66 are electrically connected to the actuator 12 that is on the substrate 20 and the microelectrodes 28 that extend from that actuator 12. Those electrical connections include connections from the substrate 20 to the substrate 18 as described herein.

A plurality of connection pads 68 are positioned on a section of the substrate 14 that extend farther from the leading edge 15 than do substrates 16 and 18. The pads 68 are positioned on a surface that faces oppositely from the interconnect board 42. Connection pads 68 are electrically connected to the actuator 12 that is on the substrate 14 and the microelectrodes 28 that extend from that actuator 12. Others of connection pads 68 are electrically connected to the actuator 12 that is on the substrate 16 and the microelectrodes 28 that extend from that actuator 12. Those electrical connections include connections from the substrate 16 to the substrate 14 as described herein.

The connection pads can be aluminum or doped polysilicon and are fabricated along with the other microstructures on each substrate. In general, they can be made out of any conductive film. Typical industrial standard is copper or gold as these metal adhere well with solder paste.

As illustrated by FIG. 2, the substrates 26 and 24 have the same dimension along the leading edge 15, the width, and the same dimension along the plane of the substrates 26 and 24 in the direction perpendicular to the leading edge, the length. For the embodiment illustrated, the width of substrates 26 and 24 is approximately 3 millimeters, and the length is approximately 5 millimeters. The substrates 22 and 20 both have a width of approximately 4 millimeters and a length of approximately 6.5 millimeters. The substrates 18 and 16 both have a width of approximately 5 millimeters and a length of approximately 8 millimeters. The substrate 14 has a width of approximately 6 millimeters and a length of approximately 9.5 millimeters. All substrates support a microactuator 12 to which forces are applied when the microelectrodes 28 are extended or retracted.

Figure 3:
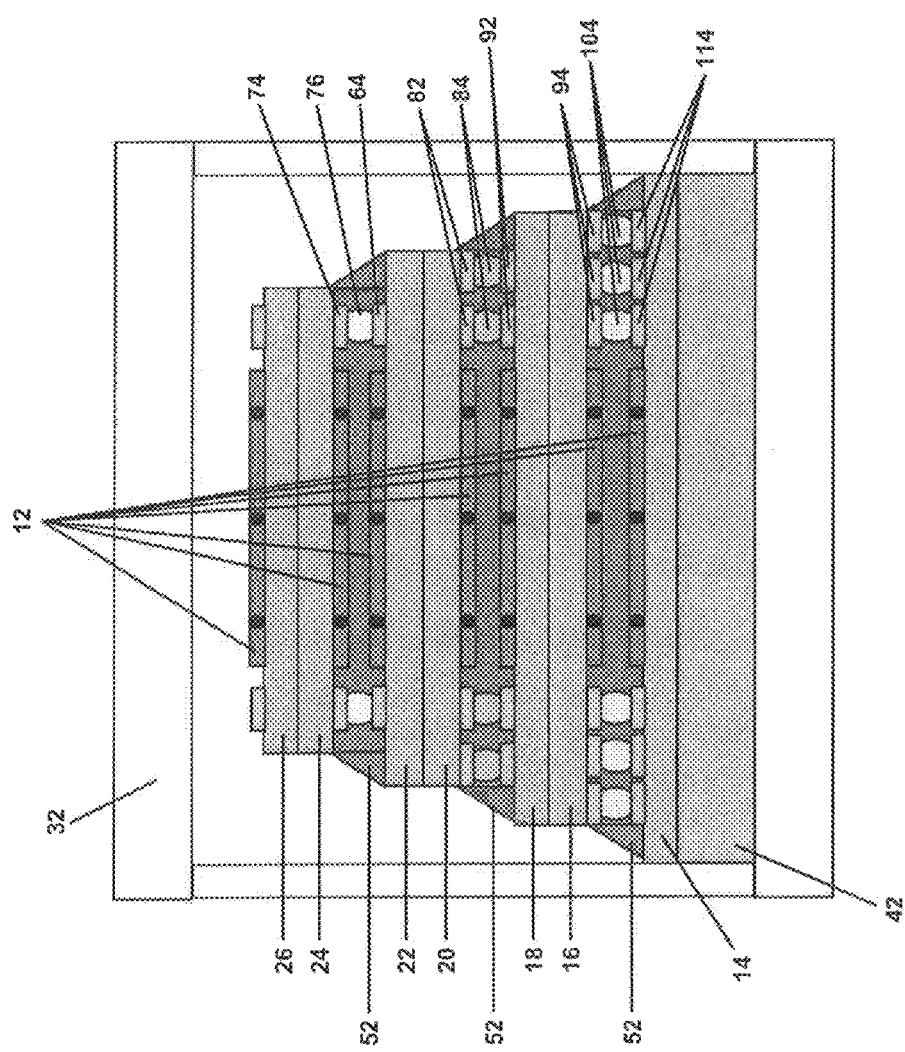
FIG. 3 is an end view of the microsensor cluster as shown by FIG. 1.

FIG. 3 shows the microsensor cluster 10 from the opening 34 in the cover 32. As shown by FIG. 3, substrate 14 includes three mounting pads 114 on the surface facing substrate 16 on opposed sides in the width direction from the microactuator 12 mounted on the substrate 14. The mounting pads 114 are spaced between the microactuator 12 and the extent of the substrate 14 in the width direction. Mounting pads 94 on the surface of substrate 16 are adjacent to and spaced from the mounting pads 114. Solder 114 adheres to opposed pairs of mounting pads 114 and 94 and spaces the substrate 16 from the substrate 14. Substrate 18 includes two mounting pads 92 on the surface facing substrate 18 on opposed sides in the width direction from the microactuator 12 mounted on the substrate 18. The mounting pads 92 are spaced between the microactuator 12 and the extent of the substrate 18 in the width direction. Mounting pads 82 on the surface of substrate 20 are adjacent to and spaced from the mounting pads 92. Solder 84 adheres to opposed pairs of mounting pads 82 and 92 and spaces the substrate 20 from the substrate 18. One of the pads 64 on the surface of substrate 22 facing substrate 24 is located on each of the opposed sides in the width direction from the microactuator 12 mounted on the substrate 22. Those pads 64 are spaced between the microactuator 12 and the extent of the substrate 22 in the width direction. Pads 74 on the surface of substrate 24 are adjacent to and spaced from the pads 64 that are outwardly adjacent to the microactuator 12 on the substrate 24. Solder 76 adheres to opposed pairs of pads 64 and 74 and spaces the substrate 24 from the substrate 22.

The substrates 14, 16, 18, 20, 22, 24 and 26 are mounted as described below to provide support the substrates to prevent deflection of the substrates and unacceptable movement of the microactuators 12 and microelectrodes 28, and to avoid stress in the substrates that will damage or cause the substrate to fail.

Figure 4:
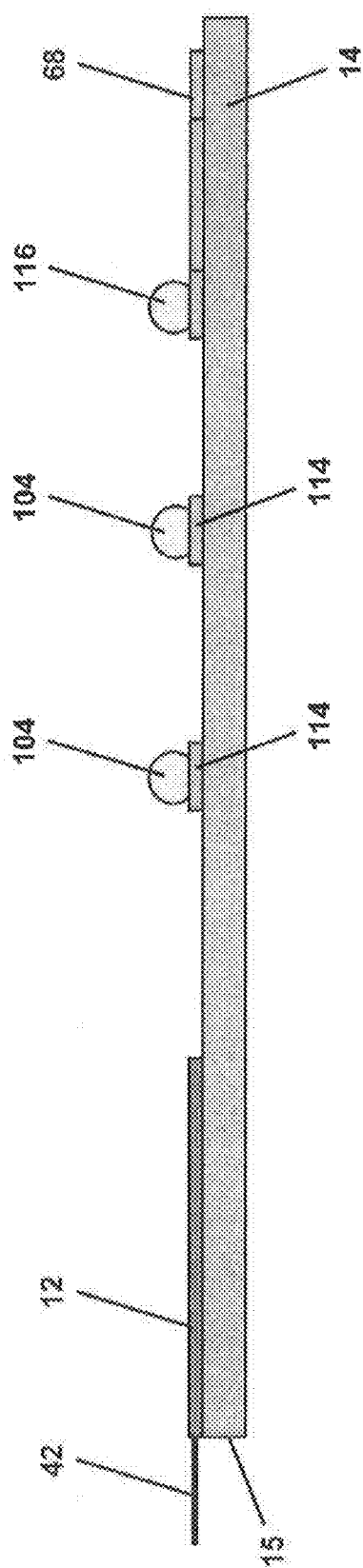
FIG. 4 illustrates the assembly created by the first step of assembly of the microsensor cluster of FIG. 1.

FIG. 4 illustrates the assembly of the first step in assembling the microsensor cluster 10. The substrate 14 is fabricated with the microactuator 12 and microelectrodes 28 on a surface of the substrate 14, two rows of mounting pads 114 on that surface extending along the width direction of the substrate 14 and the pads 68 on that surface. The two rows of mounting pads 114 are spaced from each other along the length direction of the substrate 14 and spaced from the pads 68. Signals from the microelectrodes 28 that extend from the microactuator 12 that is on the substrate 14 are received by connection pads 68 that are electrically connected to those microelectrodes 28. The microactuator 12 that is on the substrate 14 is controlled by signals provided to connection pads 68 that are electrically connected to that microactuator 12. The first step of assembly of microsensor cluster 10 comprises applying solder 104 to the pads 114 and solder 116 to pads 68. Solder is composed of flux and solder particulates, with the size of 5 to 15 μm; as typically used in the industry a 50:50 composition by volume between solder particulates and flux. Solder particulate composition is determined by what is commercially available.

Figure 5:
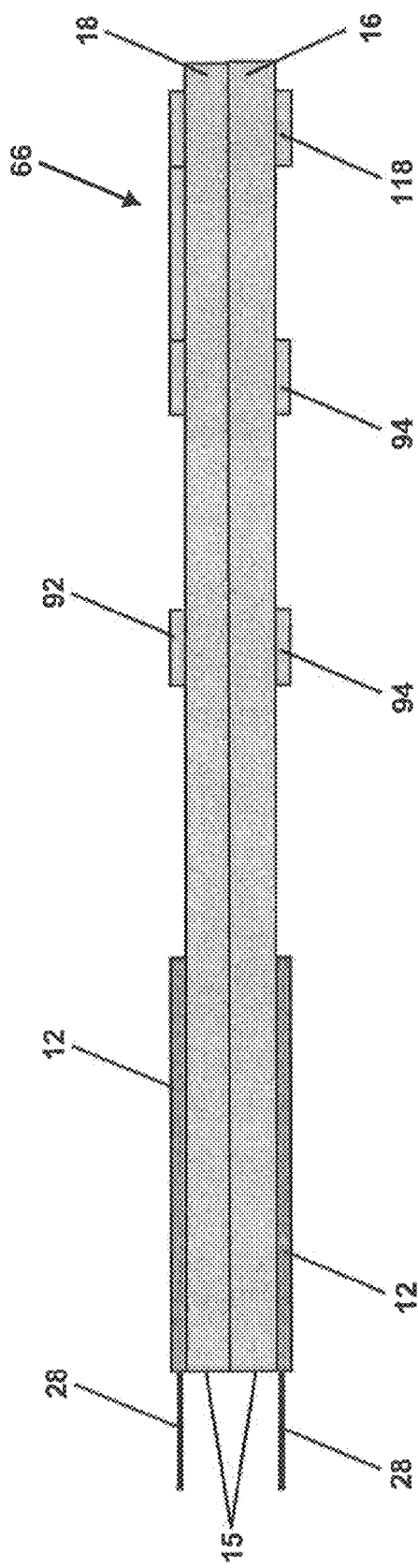
FIG. 5 illustrates the assembly created by the second step of assembly of the microsensor cluster of FIG. 1.

FIG. 5 illustrates the assembly created by the second step in assembling the microsensor cluster 10. The substrate 16 is fabricated with the microactuator 12 and microelectrodes 28 on a surface of the substrate 16, with two rows of mounting pads 94 extending along the width direction on that surface of the substrate 16 and with connection pads 118 on that surface. The two rows of mounting pads 94 are spaced from the leading edge 15 of the substrate 16 by the same distance that the rows of mounting pads 114 are spaced from the leading edge 15 of the substrate 14. As shown by FIG. 3, the pads 94 are spaced along the width direction of the substrate 16 to be adjacent to the mounting pads 114 on the substrate 14 when the substrate 16 is positioned adjacent to the substrate 14. The connection pads 118 on the substrate 16 are electrically connected to the microactuator 12 that is on the substrate 16 and to the microelectrodes 28 that extend from that microactuator 12. Signals from the microelectrodes 28 may be received by the connection pads 118 that are electrically connected to and the microelectrodes 28. The microactuator 12 on the substrate 16 may be controlled by signals provided to connection pads 118 that are electrically connected to that microactuator 12.

The substrate 18 is fabricated with the microactuator 12 and microelectrodes 28 on a surface of the substrate 18, a row of mounting pads 92 extends along the width direction on that surface of the substrate 18 and with connection pads 66 on that surface. The row of mounting pads 92 is separated from the leading edge 15 of the substrate 18 by the distance that separates the row of mounting pads 94 on the substrate 14 that is closest to the leading edge 15 of that substrate from the leading edge 15. The connection pads 66 are electrically connected to the microactuator 12 that is on the substrate 18 and to the microelectrodes 28 that extend from that microactuator 12. Signals from the microelectrodes 28 may be received by the connection pads 66 that are electrically connected to and the microelectrodes 28. The microactuator 12 on the substrate 18 may be controlled by signals provided to connection pads 118 that are electrically connected to that microactuator 12.

The substrates 16 and 18 are sized to have the same length and width. The second step of assembly of microsensor cluster 10 comprises positioning the substrates 16 and 18 adjacent to each other so that the leading edges 15 of the substrates 16 and 18 are adjacent to each other and a surface of each substrate that is opposed to the surface on which the microactuators 12 and pads are located abuts such an opposed surface of the other substrate. As shown by FIG. 5, in this position, the row of mounting pads 92 nearest the leading edges 15 is adjacent to the row of mounting pads 94 that is nearest those leading edges, the row of mounting pads 94 that is farther from the leading edges 15 and the row of connection pads 118 are adjacent to the connection pads 66. The second step of assembly of microsensor cluster 10 further comprises eutectic bonding of the substrates 16 and 18 to each other at the abutting surfaces.

Figure 6:
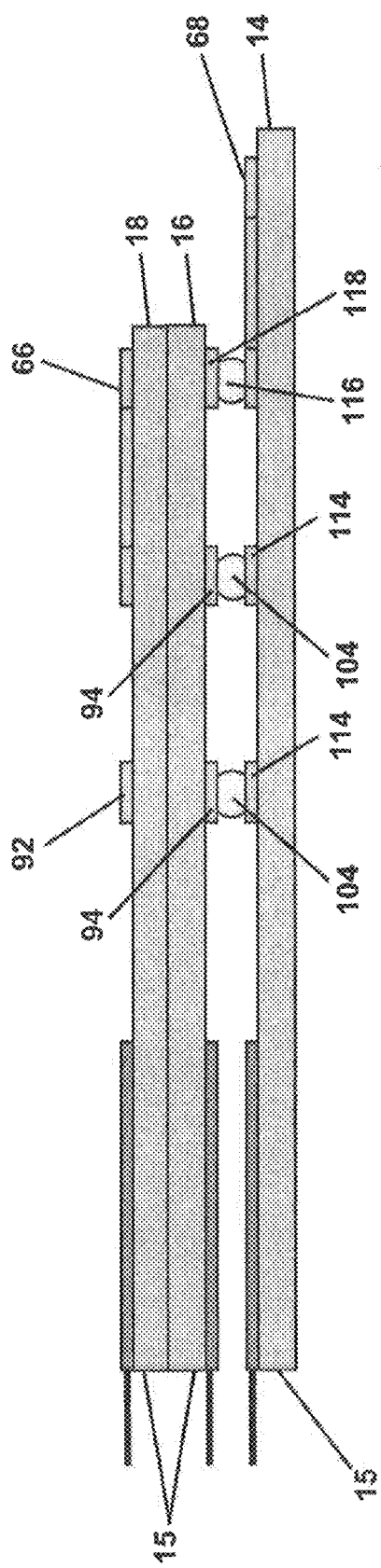
FIG. 6 illustrates the assembly created by the third step of assembly of the microsensor cluster of FIG. 1.

FIG. 6 illustrates the assembly of the third step in assembling the microsensor duster 10. The bonded substrates 16 and 18 are positioned adjacent to the substrate 14 so that the leading edges 15 of the substrates 14, 16 and 18 lie approximately in a plane and the surface of the substrate 16 on which the microactuator 12 and pads 94 and 118 are positioned overlies the surface of the substrate 14 on which the microactuator 12 and pads 114 and 68 are positioned. The mounting pads 94 are positioned adjacent to the solder 104 on the mounting pads 114 and the connection pads 118 are positioned adjacent to the solder 116 on the connection pads 68. The solder 104 and 116 bond the substrate 14 to the substrate 16 and reflow soldering creates a solder connection between mounting pads 94 and 104 and between connection pads 118 and 68.

As presently preferred, solder used for this process is manufactured by Indium Corporation and is 63 Sn and 37 Pb solder. A slow reflow process is preferably used wherein the melting temperature is approached over 60 to 80 minutes. This slow heating allows flux to evaporate preventing contamination of the active MEMS components, microactuators 12 and microelectrodes 28, by the flux which can interfere with functioning of the MEMS components.

Figure 7:
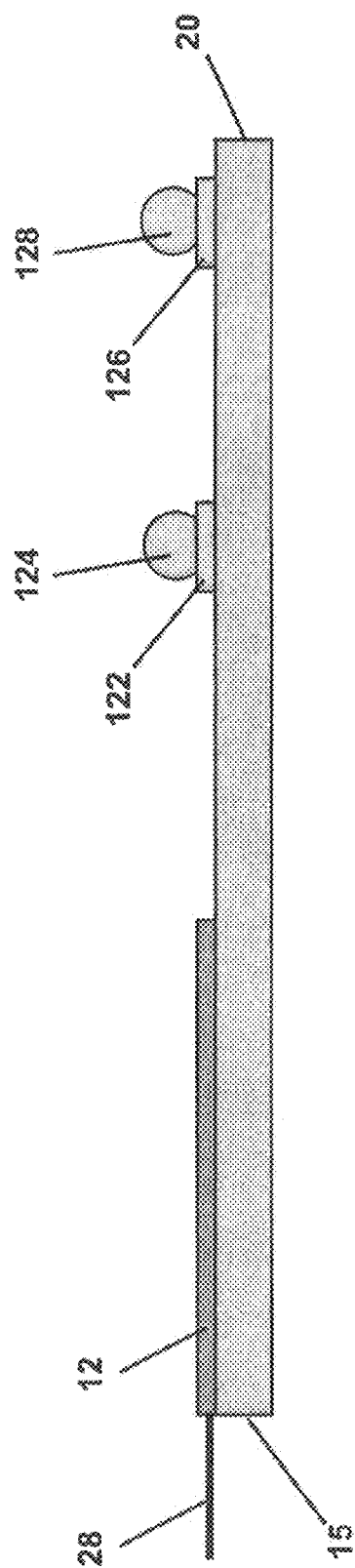
FIG. 7 illustrates the assembly created by the fourth step of assembly of the microsensor cluster of FIG. 1.

FIG. 7 illustrates the assembly of the fourth step in assembling the microsensor cluster 10. The substrate 20 is fabricated with the microactuator 12 and microelectrodes 28 on a surface of the substrate 20, with a row of mounting pads 122 on that surface extending along the width direction of the substrate 20 and a row of connection pads 126 extending along the width direction of the substrate 20. The row of mounting pads 122 is separated from the leading edge 15 of the substrate 20 by the same distance that the mounting pads 92 are separated from the leading edge 15 of the substrate 18. The connection pads 126 are separated from the leading edge 15 of the substrate 20 by a distance that is approximately the distance that the connection pads 66 are separated from the leading edge 15 of the substrate 18. The row of mounting pads 122 and the row of connection pads 126 are spaced from each other along the length direction of the substrate 20. Signals from the microelectrodes 28 that extend from the microactuator 12 that is on the substrate 20 are received by connection pads 126 that are electrically connected to those microelectrodes 28 and the microactuator 12 that is on the substrate 20 is controlled by signals provided to connection pads 126 that are electrically connected to that microactuator 12. The fourth step of assembly of microsensor cluster 10 comprises applying solder 124 to each of the mounting pads 122 and applying solder 128 to each of the connection pads 126.

Figure 8:
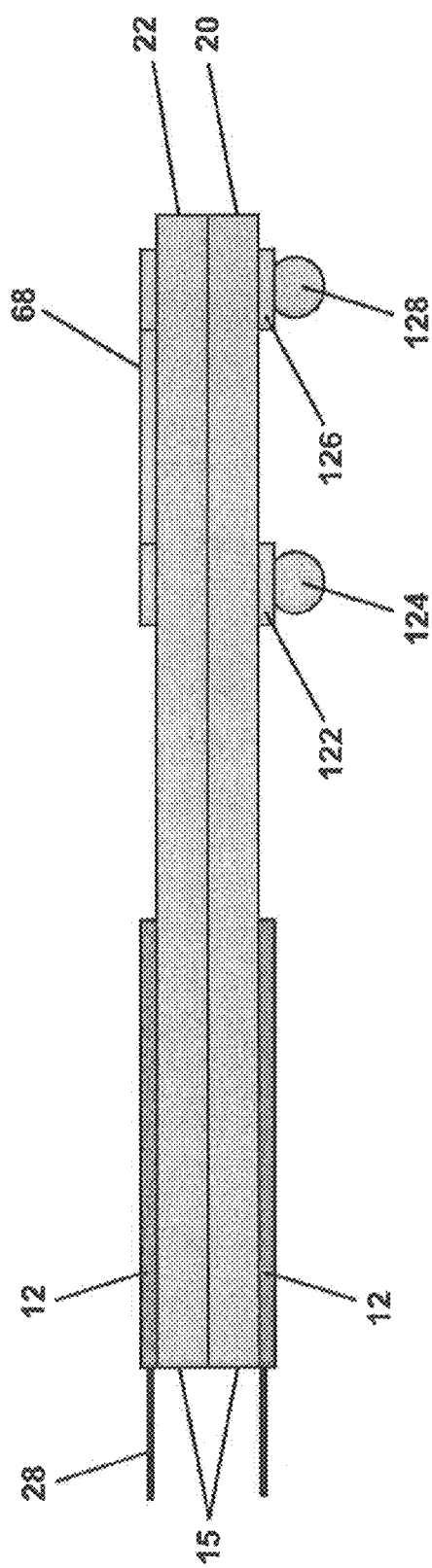
FIG. 8 illustrates the assembly created by the fifth step of assembly of the microsensor cluster of FIG. 1.

FIG. 8 illustrates the assembly of the fifth step in assembling the microsensor cluster 10. The substrate 22 is fabricated with the microactuator 12 and microelectrodes 28 on a surface of the substrate 22 with connection pads 68 on that surface and separated from the leading edge 15 of the substrate 22. The connection pads 68 are electrically connected to the microactuator 12 that is on the substrate 22 and to the microelectrodes 2.8 that extend from that microactuator 12. Signals from the microelectrodes 28 may be received by the connection pads 68 that are electrically connected to and the microelectrodes 28. The microactuators 12 on the substrate 22 may be controlled by signals provided to connection pads 68 that are electrically connected to that microactuator 12.

The substrates 20 and 22 are sized to have the same length and width. The fifth step of assembly of microsensor cluster 10 comprises positioning the substrates 20 and 22 adjacent to each other so that a surface of each substrate that is opposed to the surface on which the microactuators 12 and pads are located abuts such an opposed surface of the other substrate. The fifth step of assembly of microsensor cluster 10 further comprises eutectic bonding of the substrates 20 and 22 to each other at the abutting surfaces.

Figure 9:
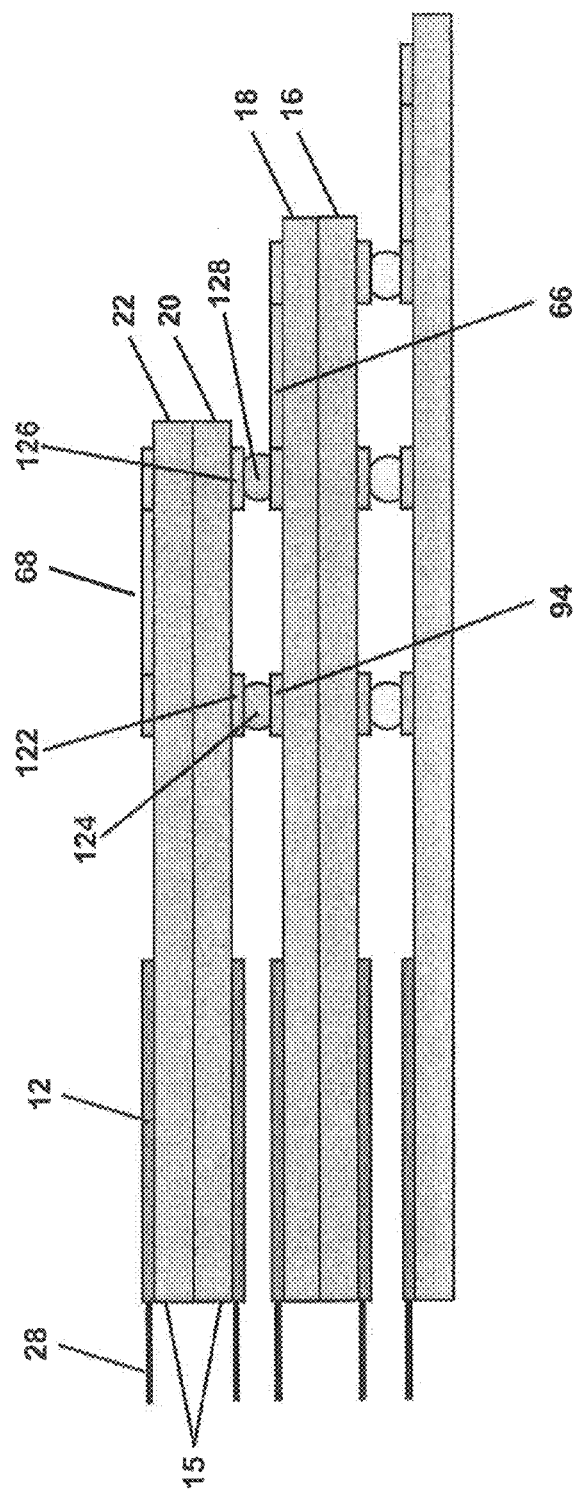
FIG. 9 illustrates the assembly created by the sixth step of assembly of the microsensor cluster of FIG. 1.

FIG. 9 illustrates the assembly of the sixth step in assembling the microsensor cluster 10. The bonded substrates 20 and 22 are positioned adjacent to the substrate 18 so that the leading edges 15 of the substrates 18, 20 and 22 lie approximately in a plane and the surface of the substrate 20 on which the microactuator 12 and pads 122 and 126 are positioned overlies the surface of the substrate 18 on which the microactuator 12 and pads 94 and 66 are positioned. The mounting pads 122 are positioned adjacent to the mounting pads 94 capturing the solder 124 therebetween and the connection pads 126 are positioned adjacent to connection pads 66 capturing the solder 128 therebetween. The substrate 20 is bonded to the substrate 18 by reflow soldering as described above.

Figure 10:
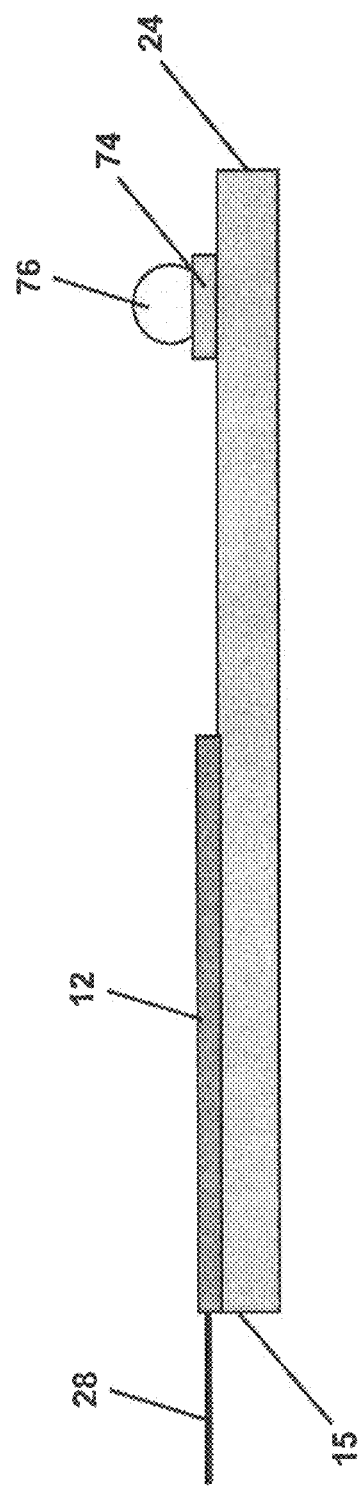
FIG. 10 illustrates the assembly created by the seventh step of assembly of the microsensor cluster of FIG. 1.

FIG. 10 illustrates the assembly of the seventh step in assembling the microsensor cluster 10. The substrate 24 is fabricated with the microactuator 12 and microelectrodes 28 on a surface of the substrate 24, with a row of connection pads 74 extending along the width direction of the substrate 24. The connection pads 74 are separated from the leading edge 15 of the substrate 24 by a distance that is approximately the distance that the connection pads 68 are separated from the leading edge 15 of the substrate 22. Signals from the microelectrodes 28 that extend from the microactuator 12 that is on the substrate 24 are received by connection pads 74 that are electrically connected to those microelectrodes 28 and the microactuator 12 that is on the substrate 24 is controlled by signals provided to connection pads 74 that are electrically connected to that microactuator 12. The seventh step of assembly of microsensor duster 10 comprises applying solder 76 to each of the connection pads 74.

Figure 11:
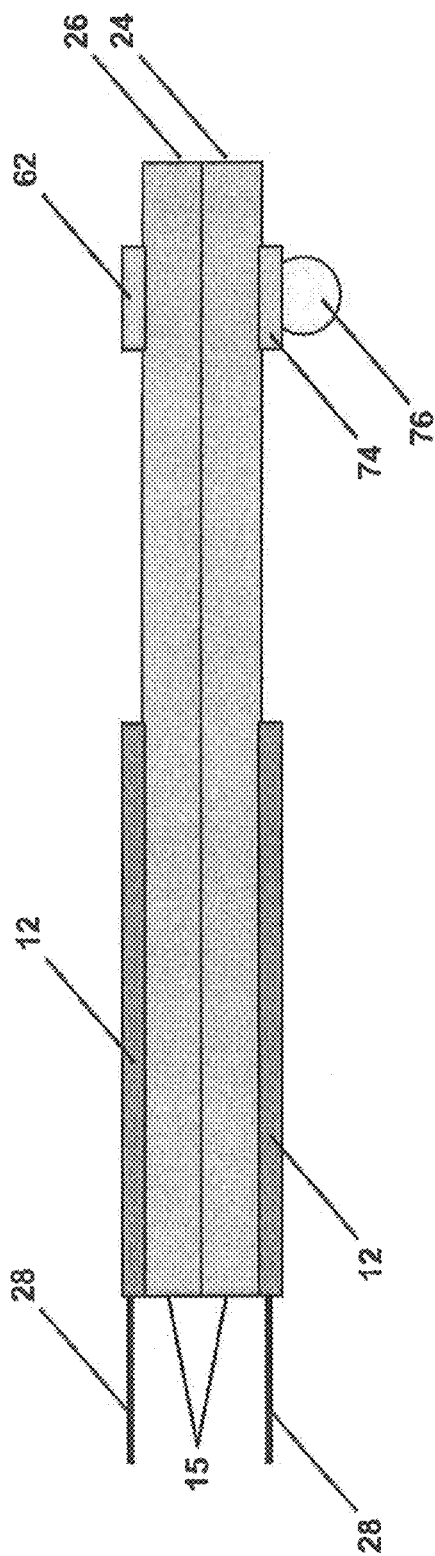
FIG. 11 illustrates the assembly created by the eighth step of assembly of the microsensor cluster of FIG. 1.

FIG. 11 illustrates the assembly of the eighth step in assembling the microsensor cluster 10. The substrate 26 is fabricated with the microactuator 12 and microelectrodes 28 on a surface of the substrate 26 with connection pads 62 on that surface and separated from the leading edge 15 of the substrate 26. The connection pads 66 are electrically connected to the microactuator 12 that is on the substrate 26 and to the microelectrodes 28 that extend from that microactuator 12. Signals from the microelectrodes 28 may be received by the connection pads 66 that are electrically connected to and the microelectrodes 28. The microactuator 12 on the substrate 22 may be controlled by signals provided to connection pads 66 that are electrically connected to that microactuator 12.

The substrates 24 and 26 are sized to have the same length and width. The eighth step of assembly of microsensor cluster 10 comprises positioning the substrates 24 and 26 adjacent to each other so that a surface of each substrate that is opposed to the surface on which the microactuators 12 and connection pads are located abuts such an opposed surface of the other substrate. The eighth step of assembly of microsensor cluster 10 further comprises eutectic bonding of the substrates 24 and 26 to each other at the abutting surfaces.

Figure 12:
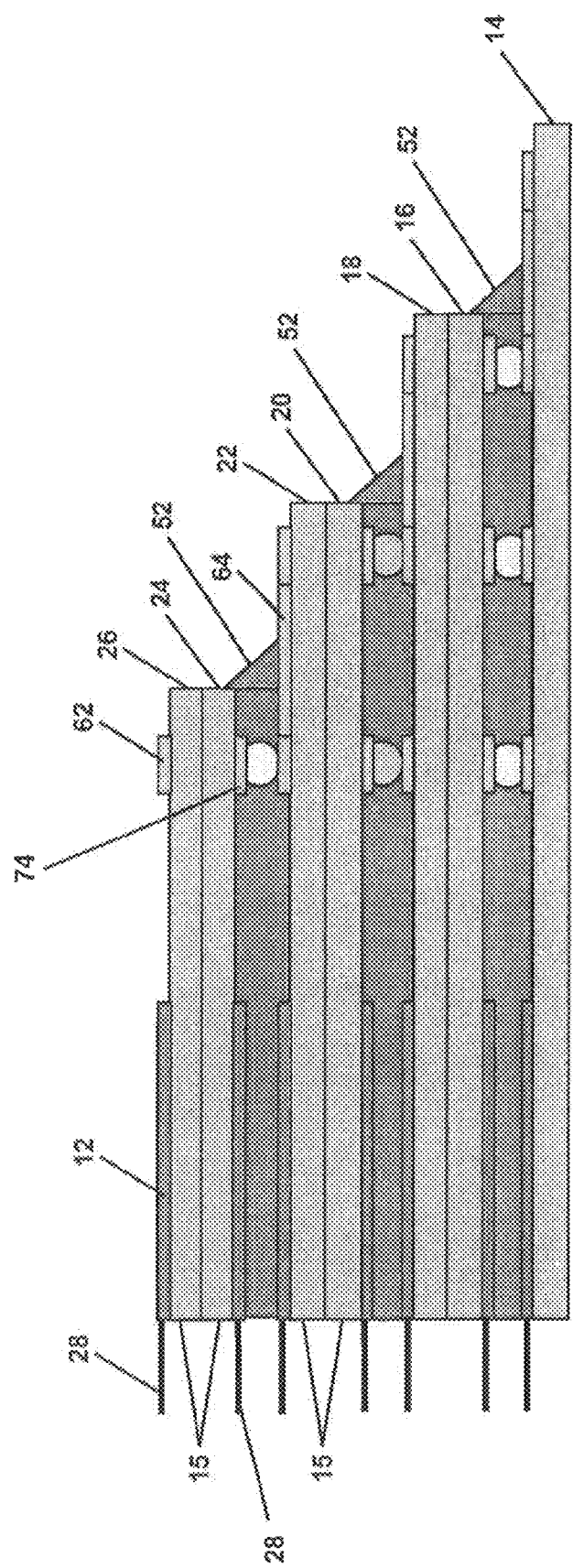
FIG. 12 illustrates the assembly created by the ninth step of assembly of the microsensor cluster of FIG. 1.

FIG. 12 illustrates the assembly of the ninth step in assembling the microsensor cluster 10. The bonded substrates 24 and 26 are positioned adjacent to the substrate 22 so that the leading edges 15 of the substrates 22, 24 and 26 lie approximately in a plane and the surface of the substrate 24 on which the microactuator 12 and connection pads 74 are positioned overlies the surface of the substrate 22 on which the microactuator 12 and connection pads 64 are positioned. The connection pads 74 are positioned adjacent to connection pads 64 capturing the solder 76 therebetween. The substrate 24 is bonded to the substrate 22 by reflow soldering as described above. The ninth step in assembling the microsensor cluster 10 further comprises applying the silicon epoxy underfill material 52 as described above. The silicon epoxy underfill material is allowed to dwell for 18 hours to assure that it is solid.

Figure 13:
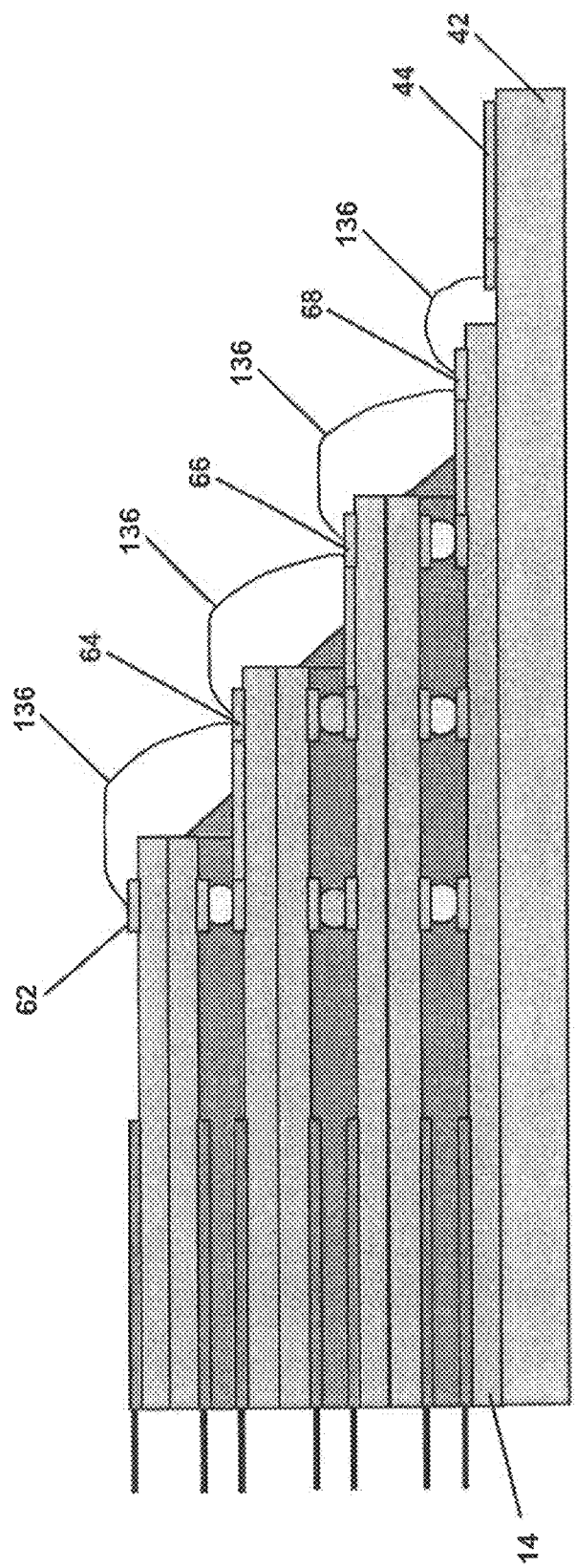
FIG. 13 illustrates the assembly created by the tenth step of assembly of the microsensor cluster of FIG. 1.

FIG. 13 illustrates the assembly of the tenth step in assembling the microsensor cluster 10. The surface of the substrate 14 that faces oppositely from the surface on which the microactuator 12, mounting pads 114 and connection pads 68 are located is positioned to overlie the interconnect board 42. The substrate 14 is adhesively bonded to the interconnect board 42. Wires 136 are then electrically connected to connection pads 62, 64, 66, 68 and 44 to provide electrical connection from the connection pads 44 to the microactuators 12 and the microelectrodes 28.

Figure 14:
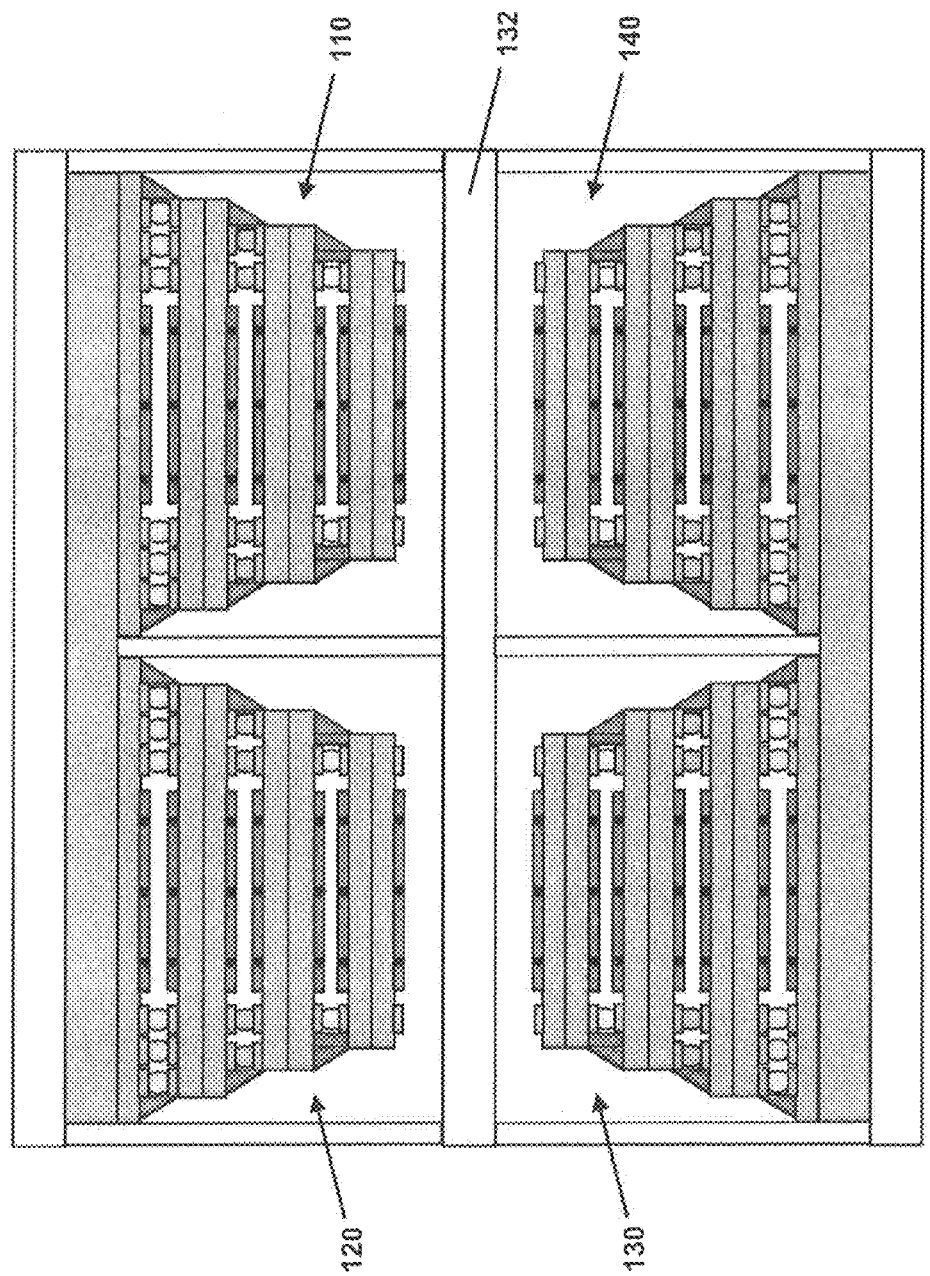
FIG. 14 is an end view of a case in which four microsensor clusters according to the present invention are supported.
Figure 15:
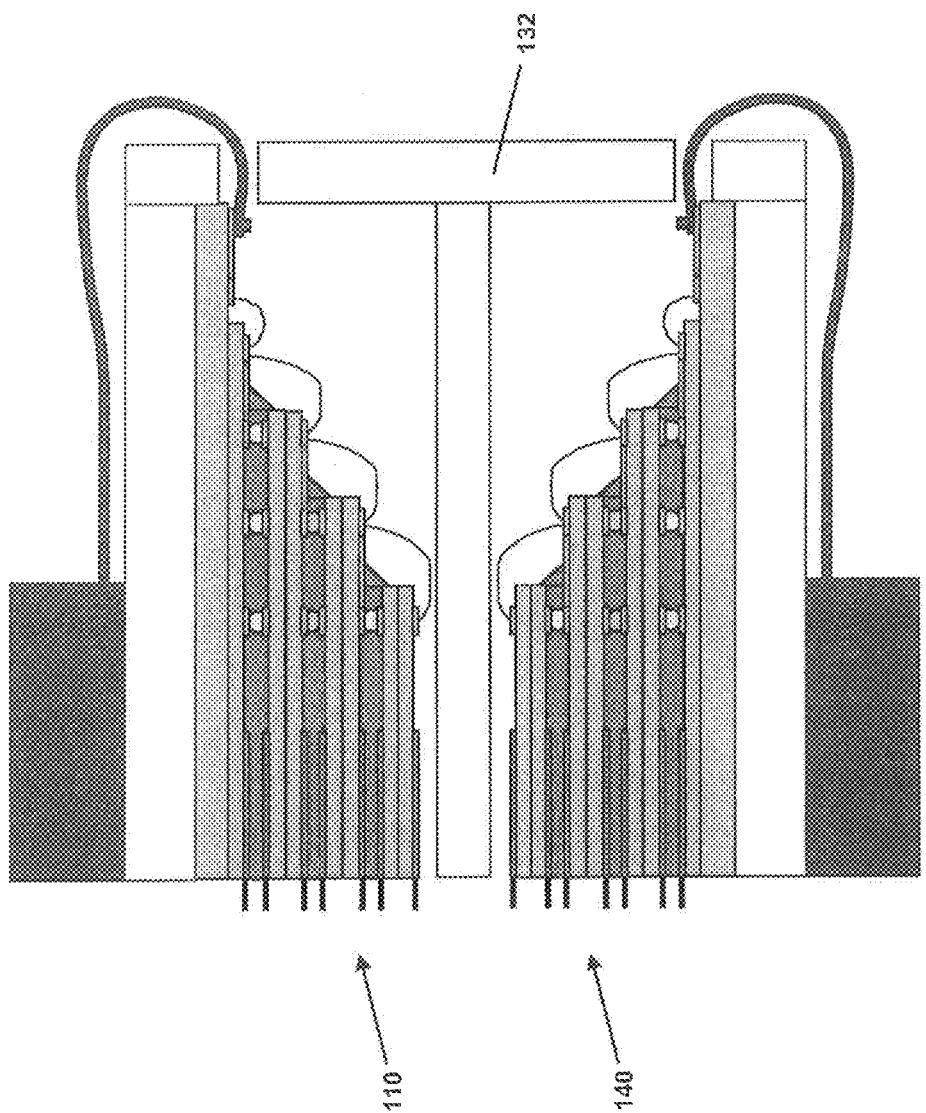
FIG. 15 is a cutaway side view of the case and microsensor clusters of FIG. 14.

FIGS. 14 and 15 show a case 132 supporting four microsensor clusters, 110, 120, 130 and 140 made in accordance with the invention. As shown, microsensor clusters may be mounted adjacent to each other to provide sensors to monitor larger regions than can be monitored by a single cluster.

Figure 16:
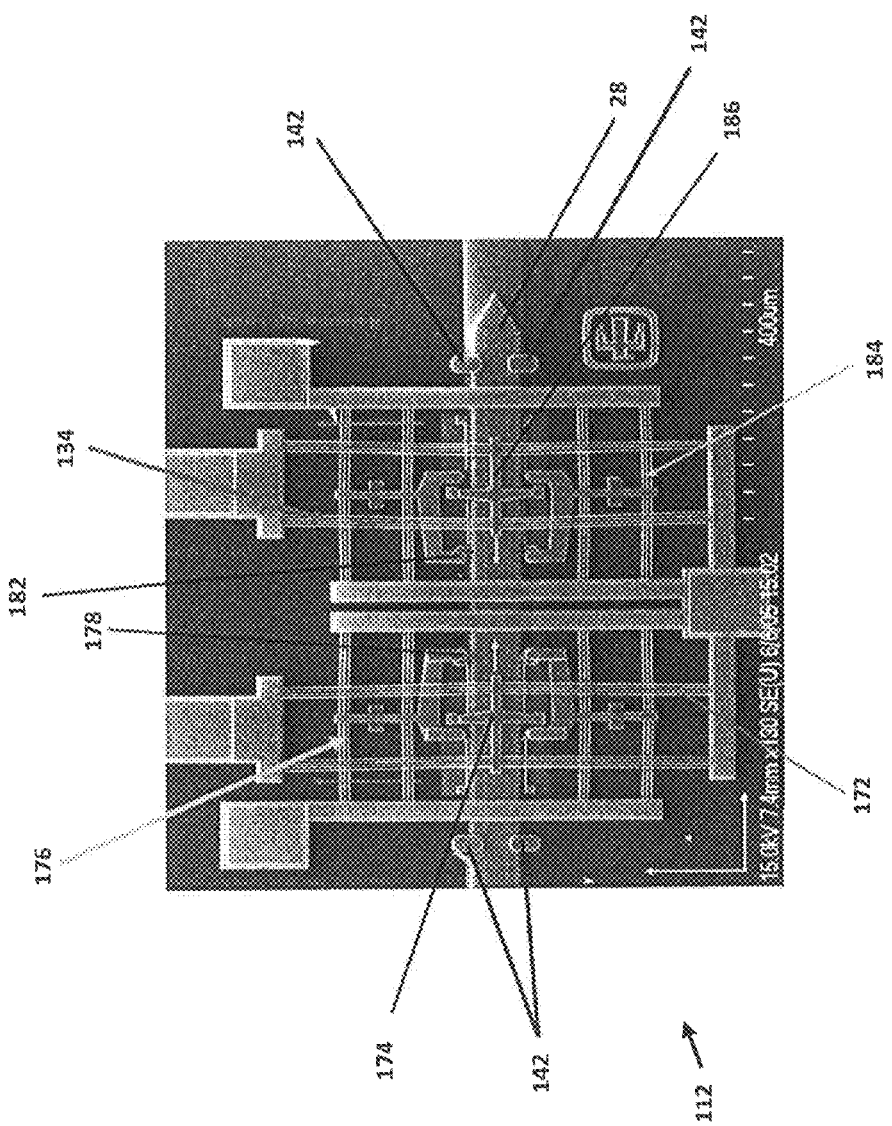
FIG. 16 is a micrograph of a microactuator that can be used in a microsensor cluster according to the invention.

FIG. 16 shows a micrograph of a 3 mm by 7 mm embodiment of a microactuator 12. The micrograph of FIG. 16 shows a mechanism 112 that includes an electrode 28 that is extended and retracted from the mechanism 112. The microactuator and microelectrodes are fabricated in Sandia National Laboratories using the SUMMiT-V process, which is a 5 layer highly doped polysilicon surface micromachining process that is described by J. Muthuswamy, M. Okandan, A. Gilletti, M. Baker, and T. Jain, "An array of microactuated microelectrodes for monitoring single neuronal activity in rodents," IEEE Trans Biomed Eng, 52:1470-1477, 2005. The microactuators have 4 thermal actuators and allow for bi-directional movement with <10 µm resolution. FIG. 16 is a SEM of a mechanism 112. The electrode 28 is 50 µm wide and 4 µm thick and can move a maximum distance of 5 mm in steps of about 8.8 µm. The mechanism 112 has a first powl 114 and a second powl 116. A move-up thermal actuator 172 causes powl 114 to translate by +X, 10 µm; when the current is off, Powl 114 elastically moves back into its original position while translates the electrode by −X, 10 µm through teeth engagement mechanism. A move-down thermal actuator unlocking mechanism 176 causes rachet 178, which normally stops the +X translation of microelectrode 28, to move in Y-direction in order to unlock the microelectrode 28. A move-up unlocking mechanism thermal actuator 184 causes rachet 182, which normally stop the −X translation of the electrode 28, to move in Y-direction in order to unlock the electrode 28. A move down thermal actuator 134 causes powl 116 to translate by −X, 10 µm; when the current is off, the arrow elastically moves back into its original position while translates the electrode by −X, 10 µm through teeth engagement mechanism. Translation guides 142 align and guide the microelectrode 28.

Figure 17:
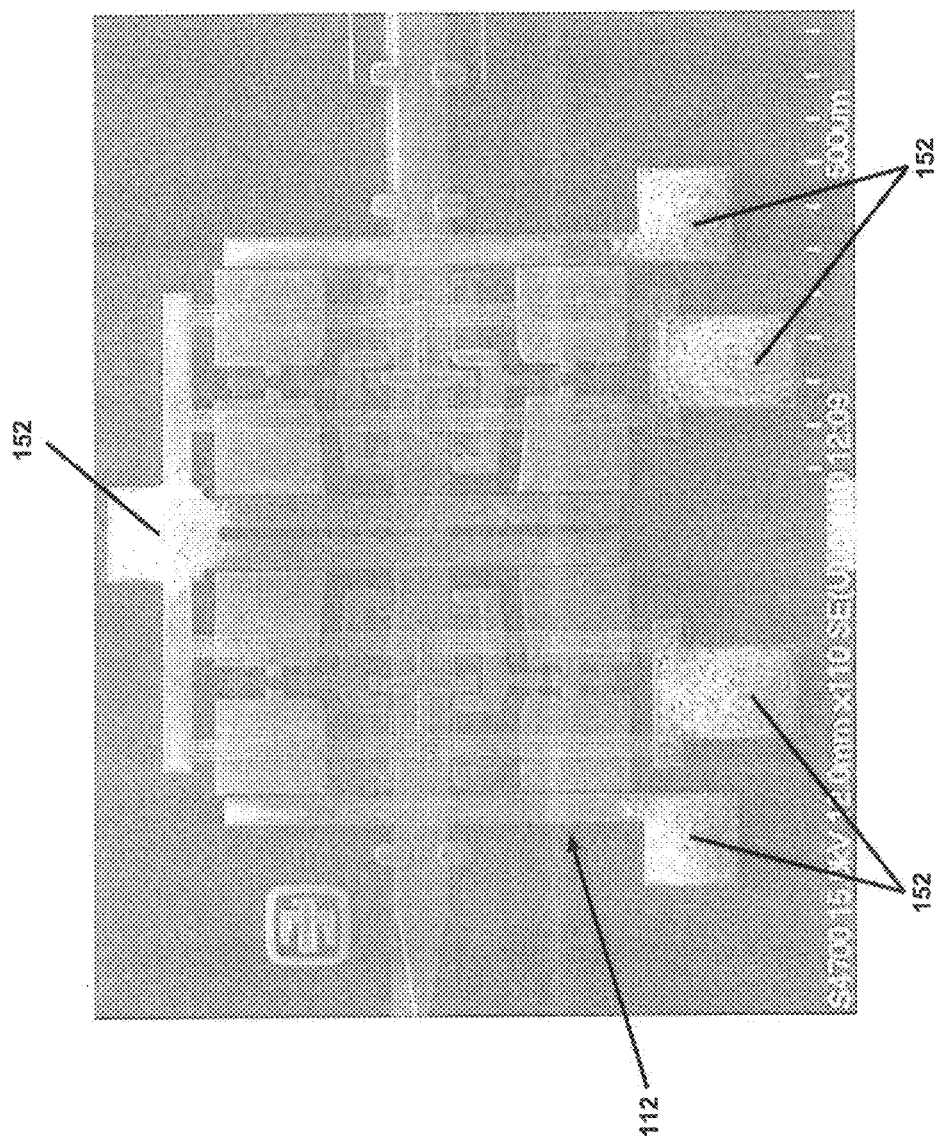
FIG. 17 shows the microactuator of FIG. 16 with solder bumps applied.
Figure 18:
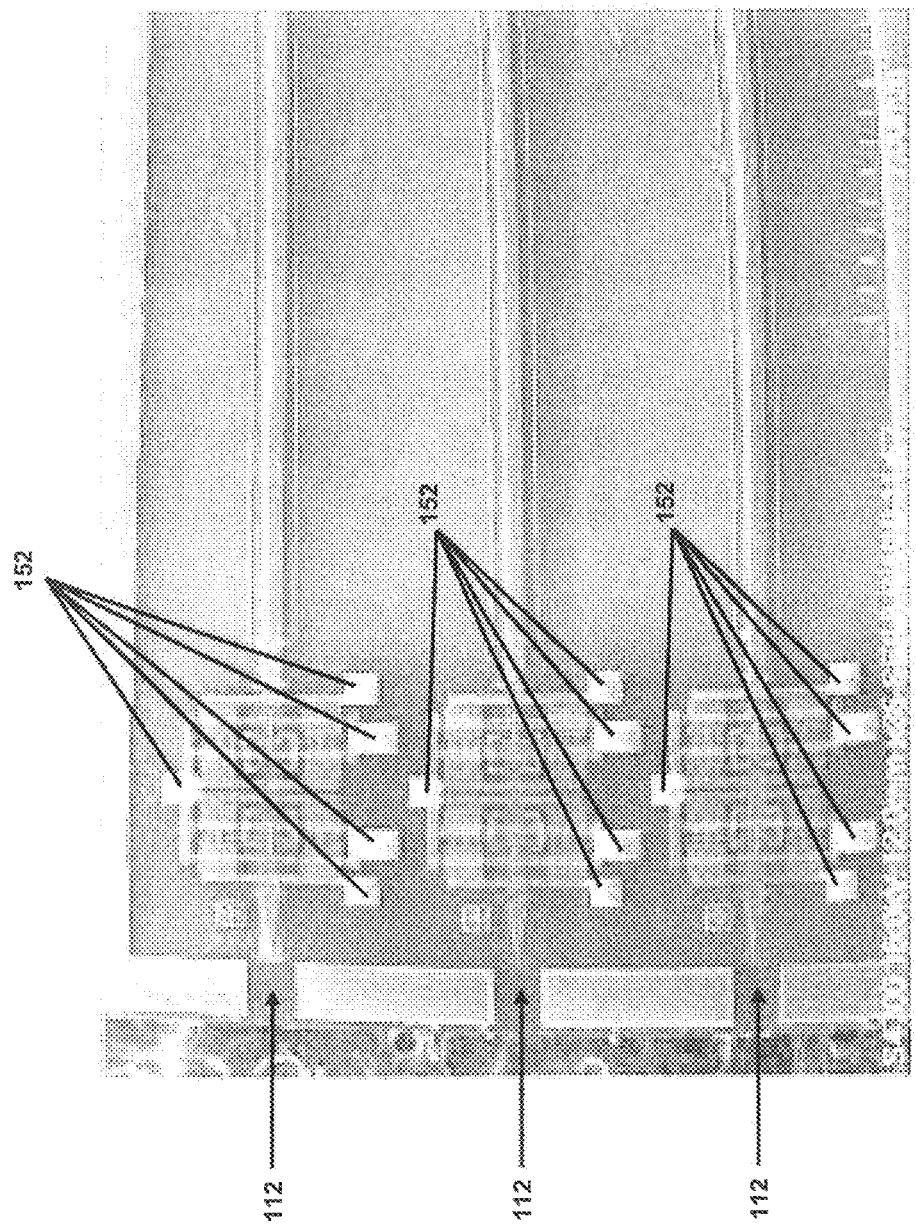
FIG. 18 shows three actuators as shown by FIG. 16 arranged in a cluster.

Packaging and interconnects contribute significant additional weight to the microactuators 12. The chip itself weighs about 0.18 g and packaging can add about ten times this weight. In an effort to miniaturize implantable devices MEMS technology is used to provide a packaging that is compact and light-weight. Flip-chip technique provides excellent solution with compact form factor. There exist special challenges to adapt this technique for MEMS devices: (a) Head-space for movement due to the presence of actuators, movable electrodes, (b) Contamination free process so that the moving parts are not obstructed (c) Semi-hermetic seal that allows for the movement of the microelectrodes outside the die as well as keeps blood and CSF fluids from entering the chip. Bumps of Ag epoxy bumps having a diameter of 50 µm diameter that avoid flux contamination are used. FIG. 17 is a SEM of a mechanism 112 having Ag epoxy bumps 152. FIG. 18 shows a microactuator 12 after the bumping process is complete on the entire chip.

Figure 19:
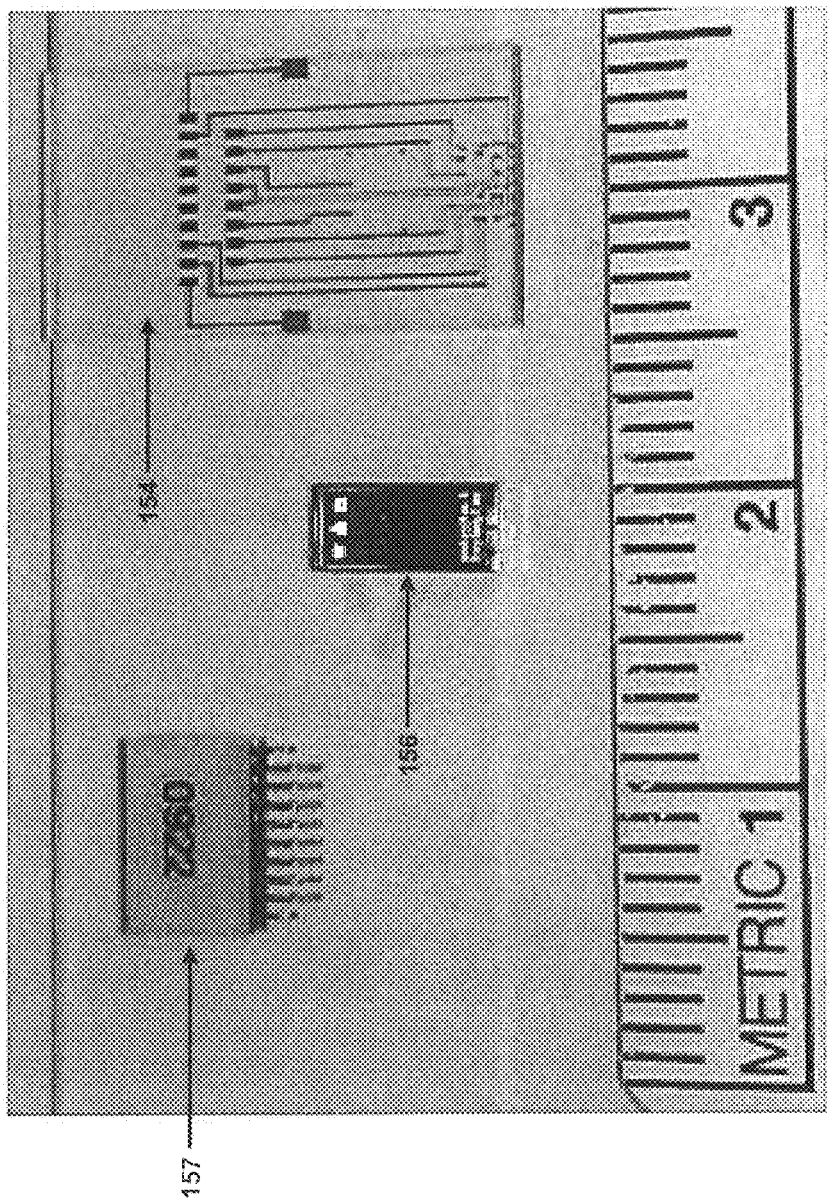
FIG. 19 shows components of a microactuator that may be incorporated in to a microsensor cluster according to the invention.
Figure 20:
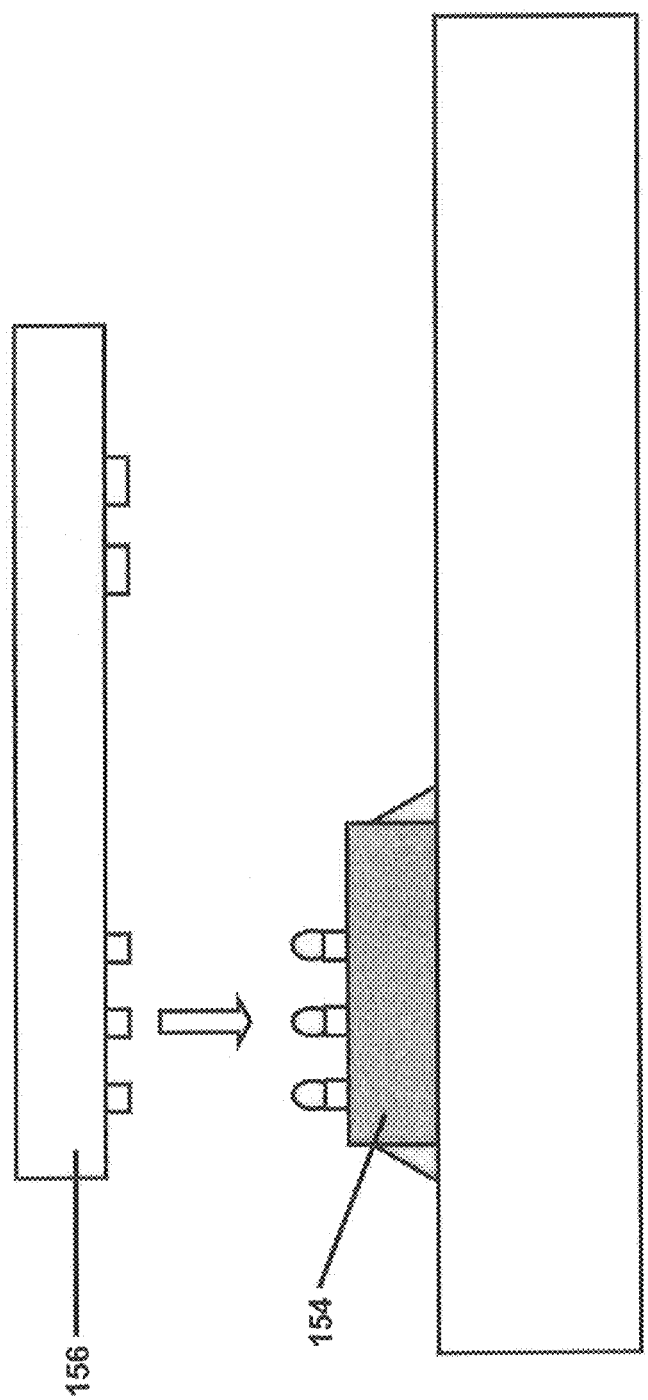
FIG. 20 depicts connection of a MEMS component to a substrate for use according to the invention.
Figure 21:
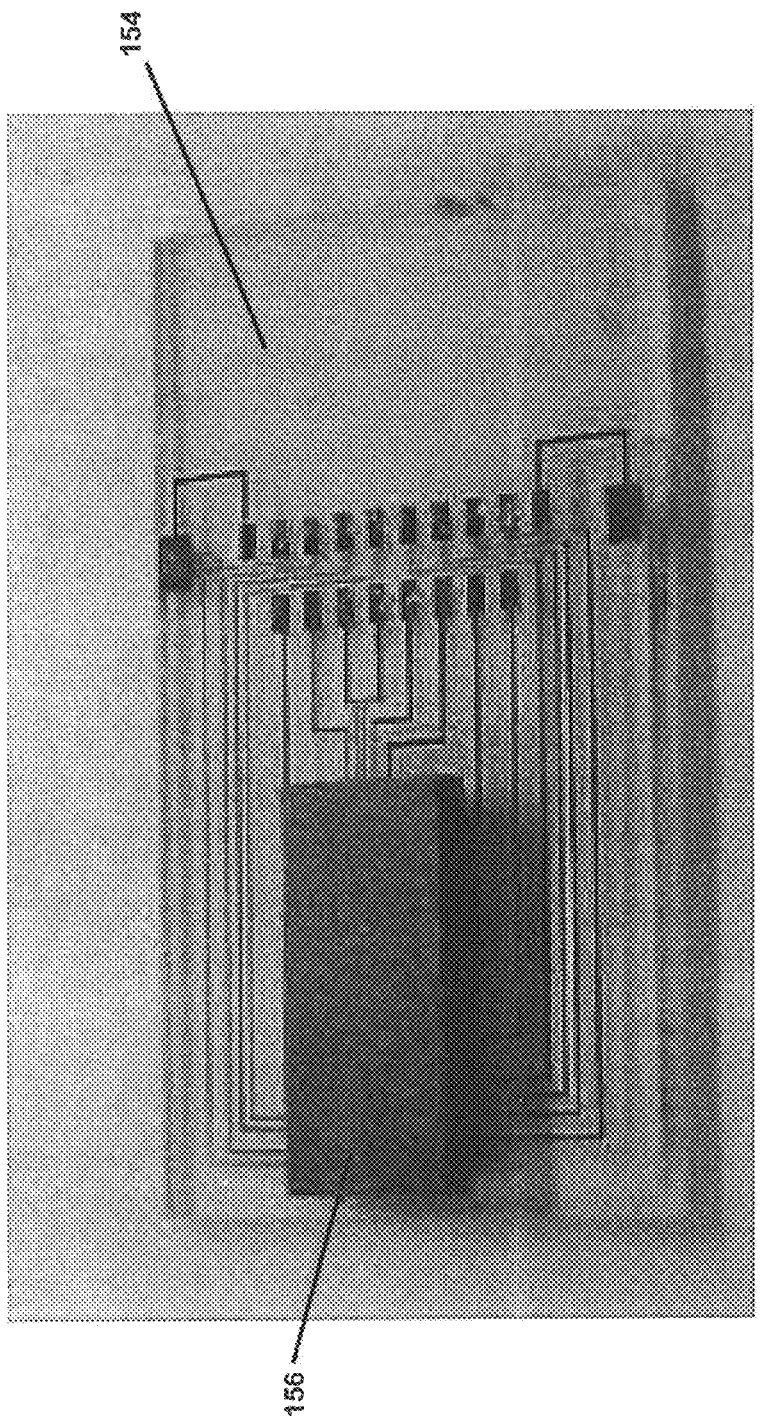
FIG. 21 shows a MEMS component mounted to at substrate for use according to the invention.
Figure 22:
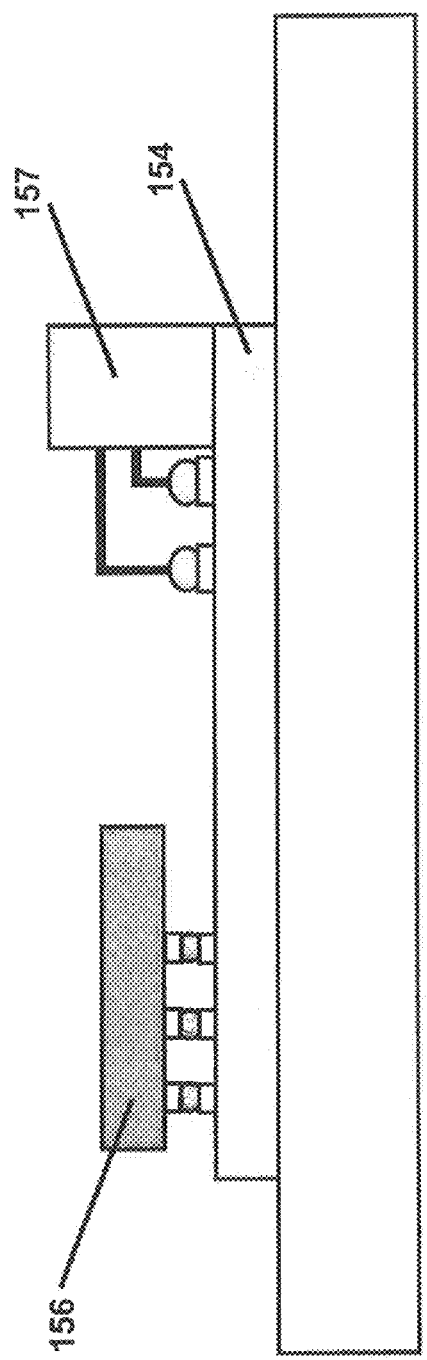
FIG. 22 is a side view of a MEMS component and a connector both mounted to at substrate for use according to the invention.
Figure 23:
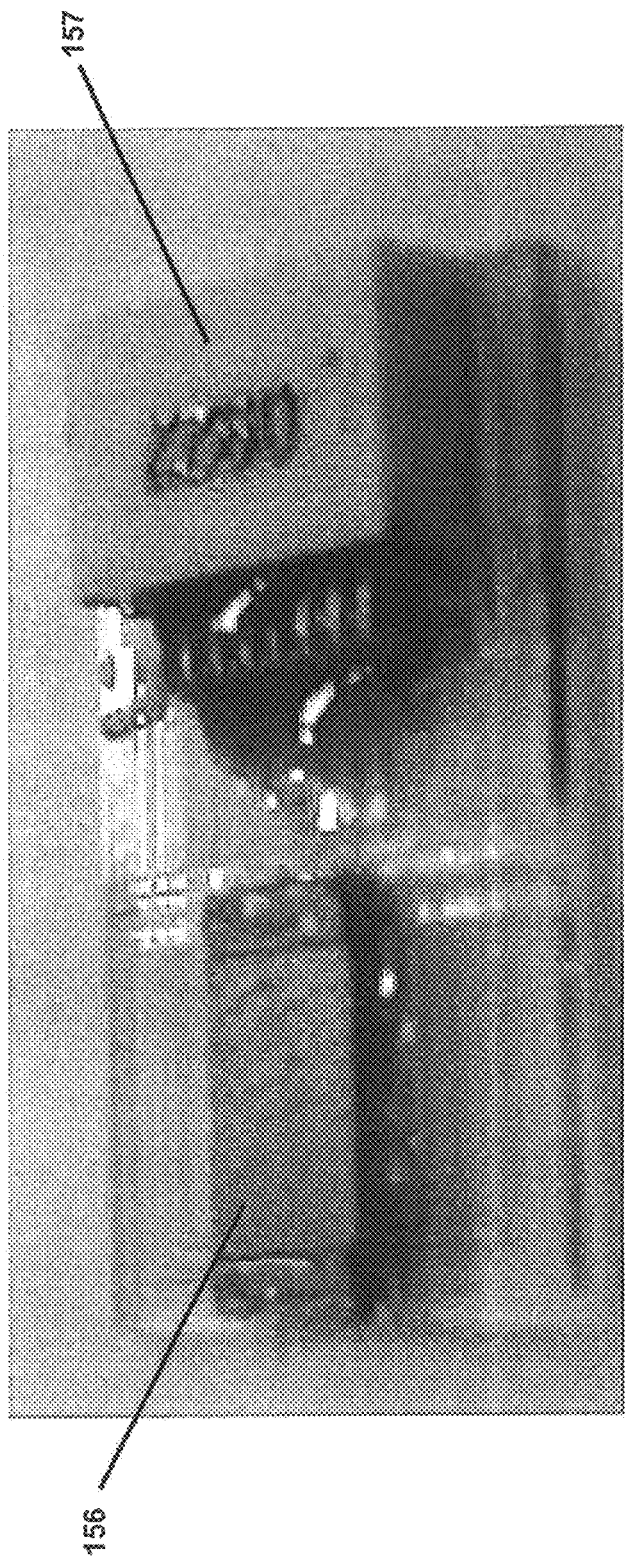
FIG. 23 is a photograph of a MEMS component and a connector both mounted to a substrate.
Figure 24:
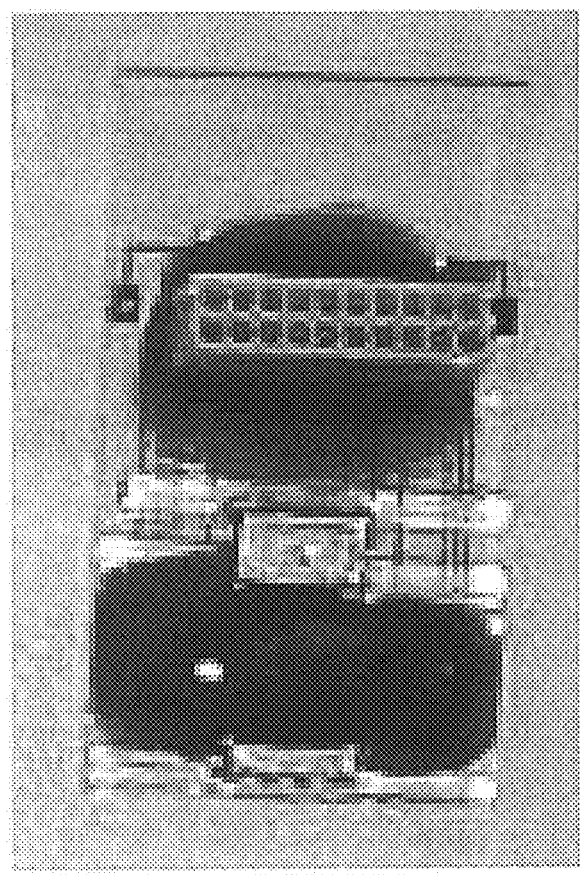
FIG. 24 is a photograph of the assembly shown by FIG. 23 with a protective sealant coating.

Assembly of an embodiment of microactuator 12 is illustrated by FIGS. 19 through 24. FIG. 19 illustrates the kitting step. A glass substrate 154 is fabricated with the corresponding bond pads as the MEMS chip and interconnects. Au is deposited through thermal evaporation (200 µm) and patterned to form the flip-chip substrate. MEMS chip 156 with Ag epoxy bumps and TLI (Third Level Interconnect) 158 are assembled. Ag epoxy bumps are deposited on the MEMS chip 156 as illustrated by FIG. 17. Flip-chip connecting joins the 500 µm glass substrate 154 to the MEMS chip 156 as shown by FIGS. 20 and 21. TLI 157 is joined to the glass substrate 154 using Ag epoxy as illustrated by FIG. 22. As illustrated by FIG. 23, the assembly is sealed by a semi-hermetic and hermetic seal-chip with semi-hermetic seal on one edge and hermetic seal on the other three sides using non-flow silicone. A hard protection is provided by applying epoxy sealant to protect the package as shown by FIG. 24.

Figure 25:
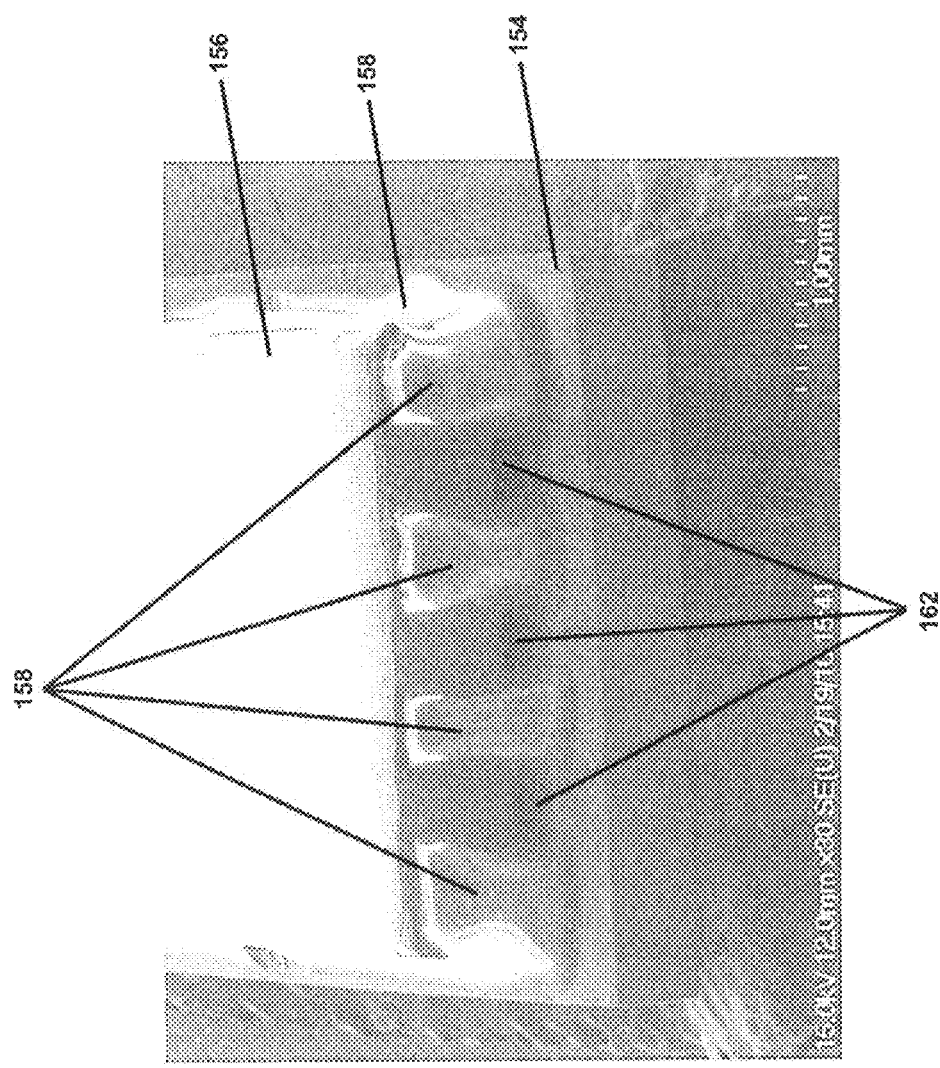
FIG. 25 is an SEM image of a MEMS chip mounted to a substrate with a seal material for use according to the invention.
Figure 26:
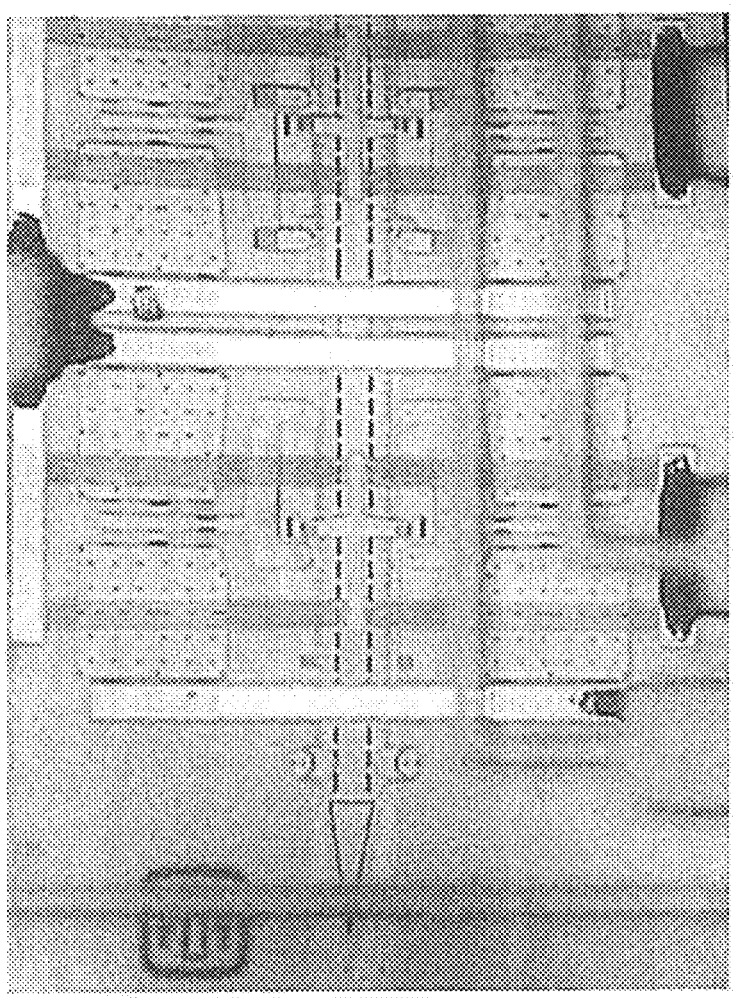
FIG. 26 is a micrograph that shows a microactuator after assembly for use according to the invention.

FIG. 25 shows the MEMS chip 156 mounted to a glass substrate 154 with the semi-hermetic and hermetic non-flow silicone seal 158. The semi-hermetic seal is adjacent to three channels 162 within which the microelectrodes 28 move freely. FIG. 26 is a micrograph that shows no flux contamination on the active MEMS structures after the flip chip process. The flip-chip technique creates an assembly that is 7 mm×9 mm and weighs approximately 0.5 g.

Figure 27:
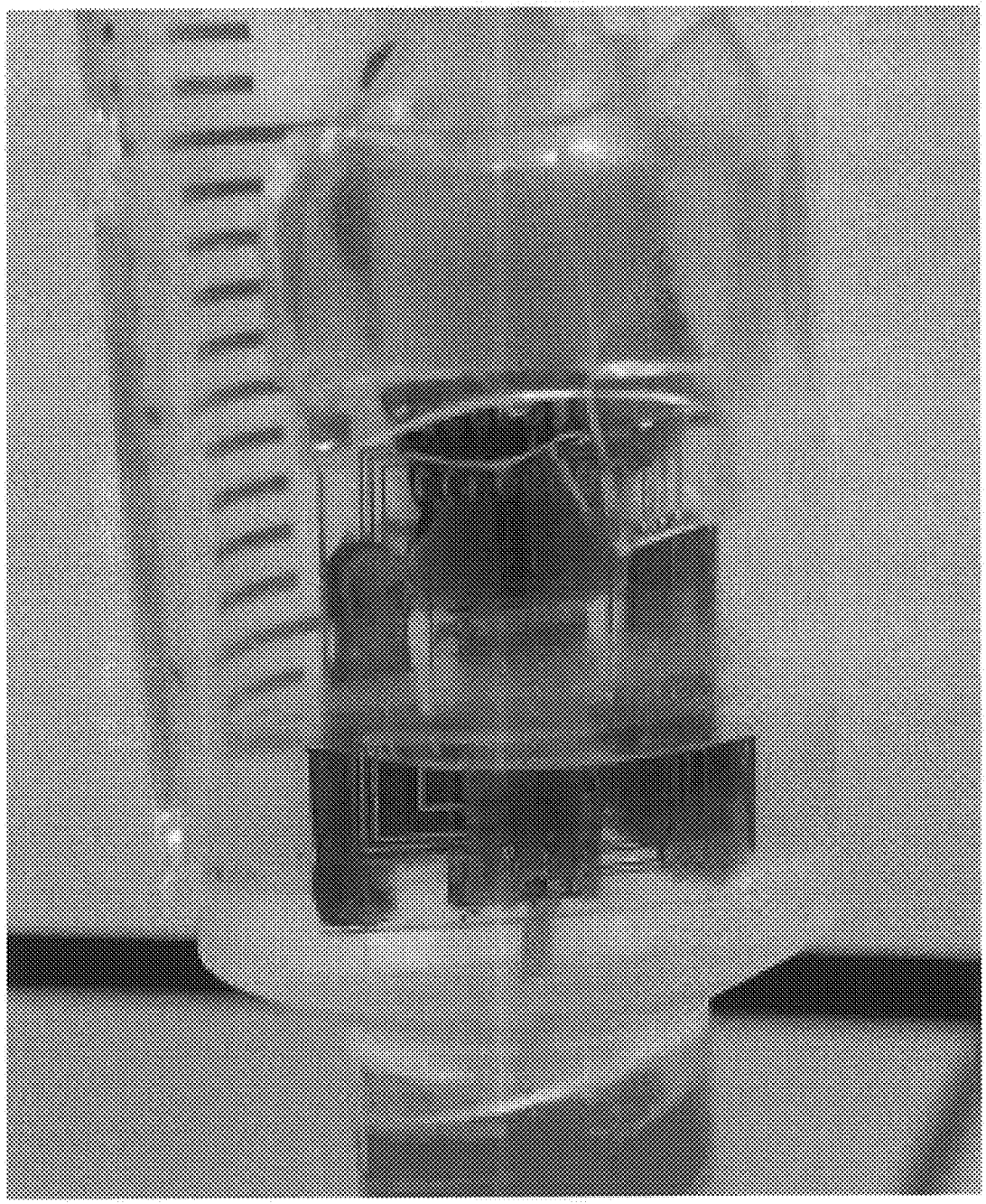
FIG. 27 is a photograph that shows a leak test of a microactuator that is sealed for use as a neural sensor according to the invention.

FIG. 27 shows a static pressure test of the assembly. The assembly was immersed in saline after the semi-hermetic seal was applied. The seal was shown to block fluid entrance at the maximum pressure of 80 cm of water, or about 7.8 kPa. At the pressure of 80 cm of water, trace of fluid leak start to leak into the channel.

Figure 28:
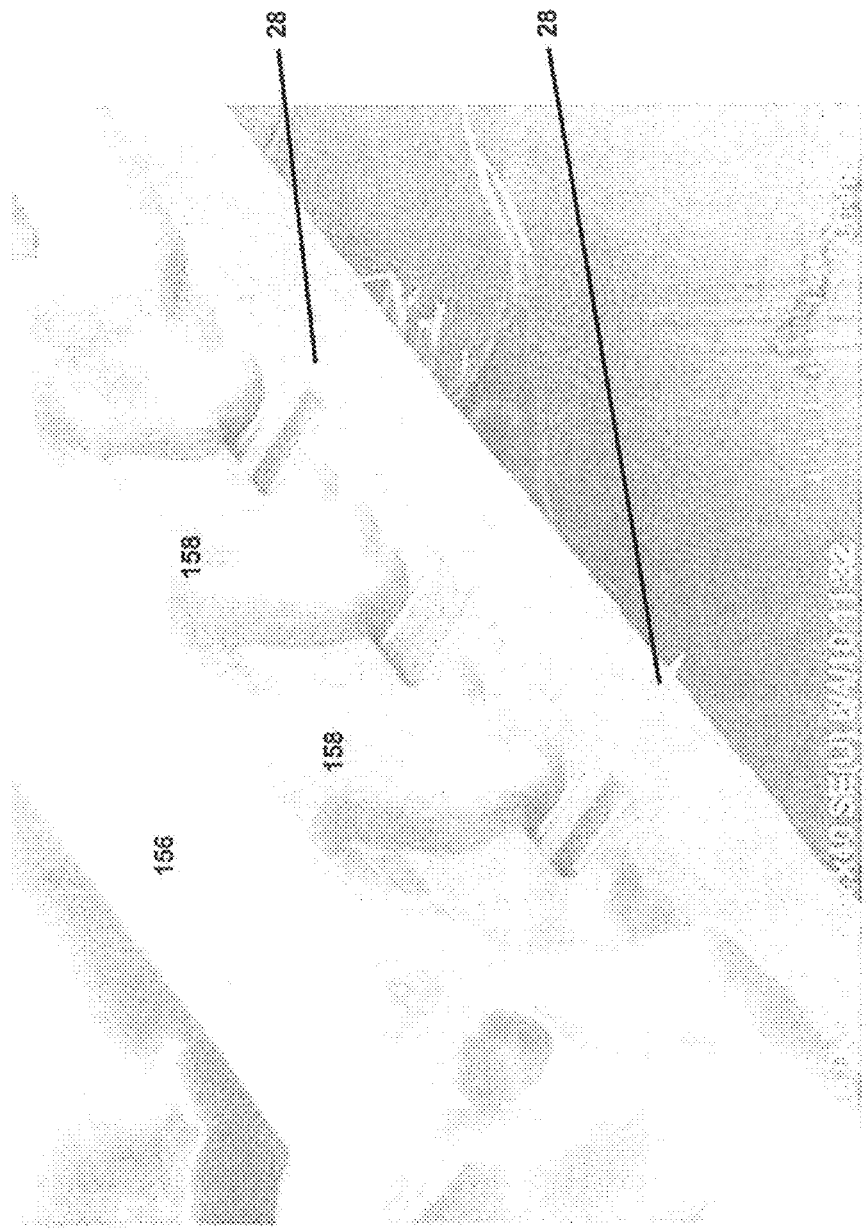
FIG. 28 is an SEM image of a microactuator with sealant for use as a neural sensor according to the invention.
Figure 29:
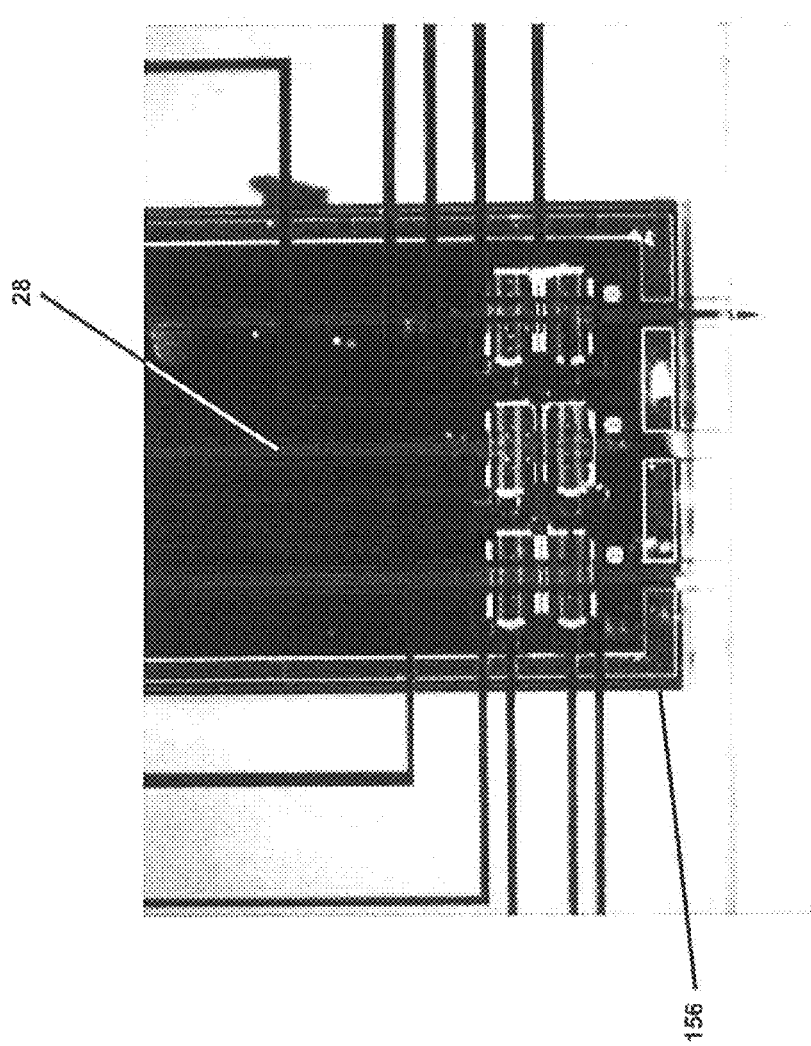
FIG. 29 is a micrograph of a microactuator having a retracted microelectrode.
Figure 30:
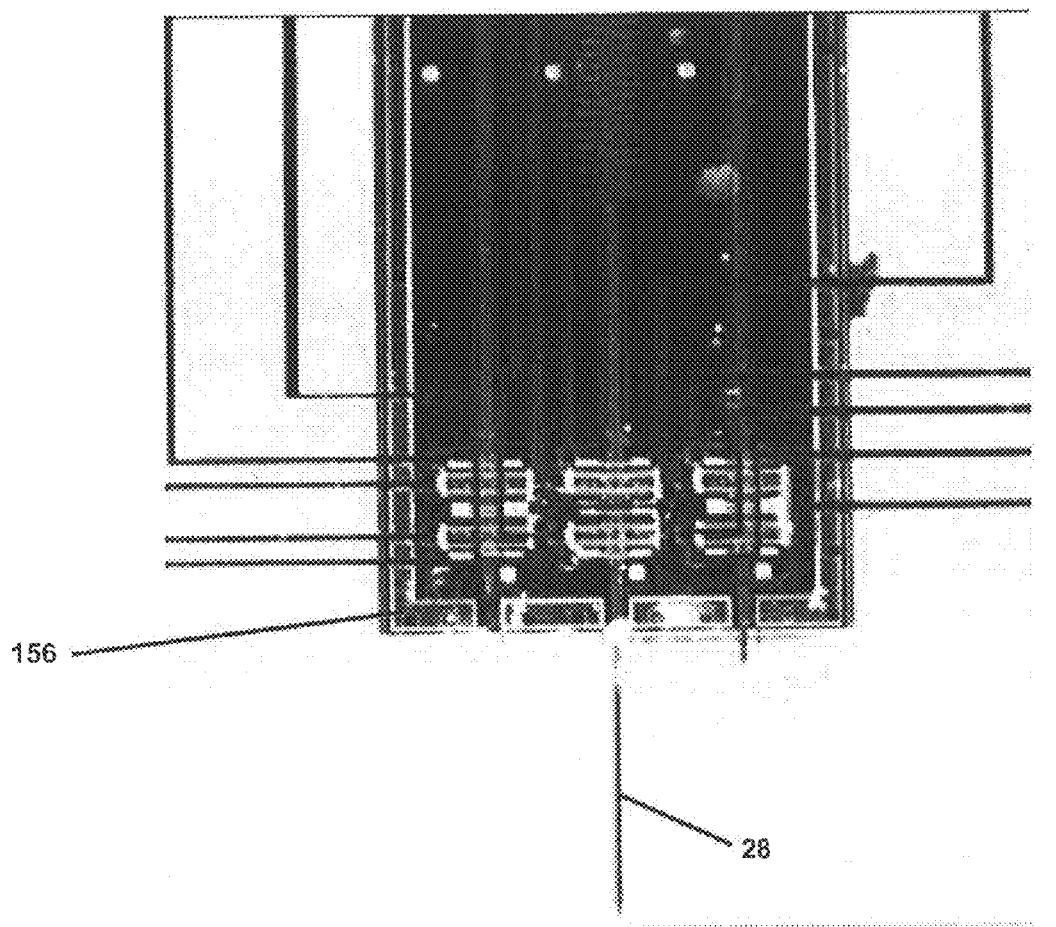
FIG. 30 is a micrograph of a microactuator having an extended microelectrode.

FIGS. 28-30 show movement of microelectrodes 28 from the MEMS chip 156. FIG. 28 is a SEM of right and left microelectrodes 28 extending from the channels in the semihermetic seal 158. FIG. 29 is a micrograph showing the middle electrode 28 of MEMS chip 156 before actuation. FIG. 30 is a micrograph showing the middle electrode 28 extended after actuation. Note that the spring that tethers the electrode to the bond-pad for electrical recording is also extended.

Figure 31:
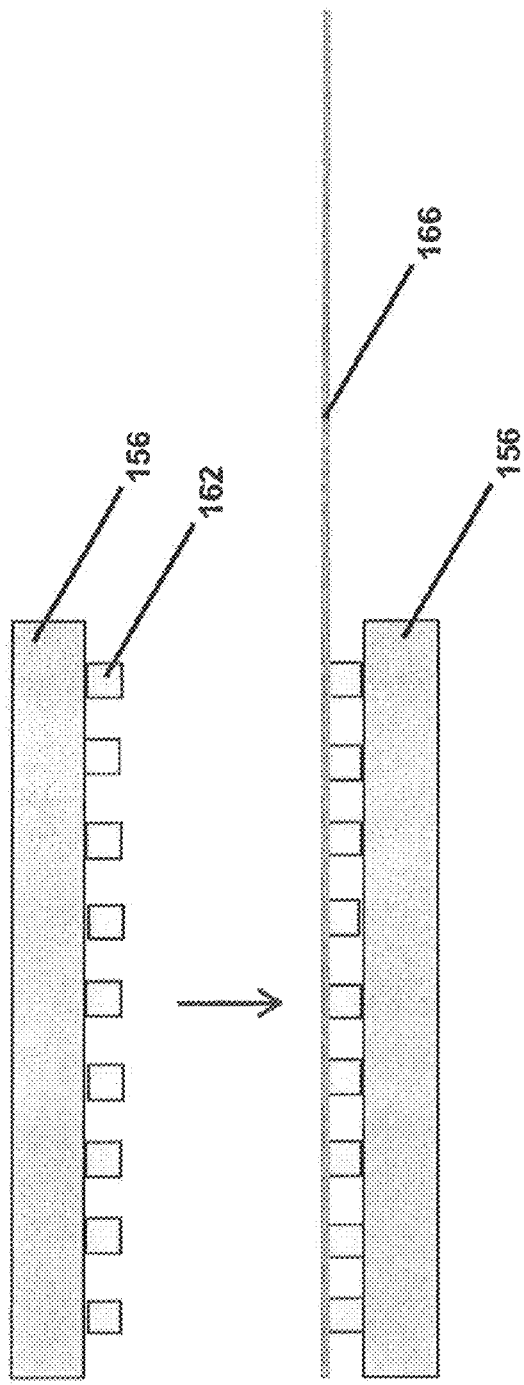
FIG. 31 is a side view of assembly of a MEMS chip with a flexible interconnect.
Figure 32:
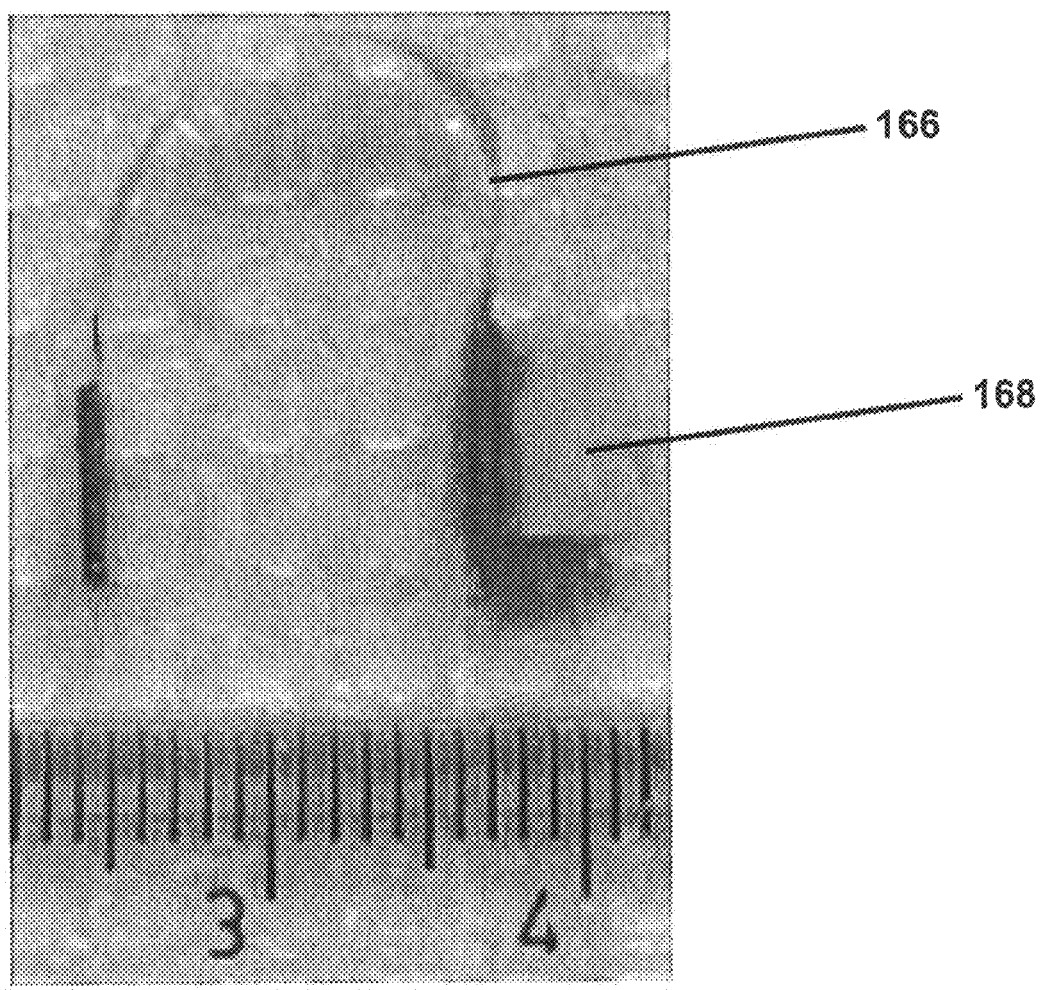
FIG. 32 is a side view of a MEMS chip connected to a connector by a flexible interconnect.

The force exerted on neural implants during insertion and removal of interconnects can be significant, and can eventually can lead to implant failure. In order to isolate these forces from the MEMS chip, a flexible parylene interconnect has been developed. These flexible interconnects makes the form factor of the package even smaller comparable to the actual chip itself. The flip chip technique described above can be adapted to bond the MEMS chip to parylene flexible substrate. FIG. 31 shows a MEMS chip 156 with Ag epoxy bumps 162, and a parylene substrate 166 is connected by flip-chip connection to the Ag epoxy bumps on the MEMS chip 156. FIG. 32 shows a complete packaged MEMS chip with flexible parylene interconnect 166 connecting the MEMS chip 156 to a connector 168.

Apparatus according to the present invention is not limited to use with a particular instrument. The invention can be adapted to a variety of clusters of MEMS components. Possible applications include MEMS sensors, MEMS gyroscope, MEMS accelerometers.

What is claimed is:

1. A three dimensional stack of active MEMS devices, the stack comprising:
a first substrate, the first substrate having:
a mounting surface,
an active MEMS device on the mounting surface,
a plurality of pads formed on the mounting surface, and
a back surface facing away from the mounting surface;
a second substrate, the second substrate having:
a mounting surface,
an active MEMS device on the mounting surface,
a plurality of pads formed on the mounting surface, and
a back surface facing away from the mounting surface;
a third substrate, the third substrate having:
a mounting surface,
an active MEMS device on the mounting surface, and
a plurality of pads formed on the mounting surface,
wherein the back surface of the second substrate is abutting and bonded to the back surface of the first substrate,
wherein the mounting surface of the second substrate is facing the mounting surface of the third substrate,
wherein the pads on the mounting surfaces of the second and third substrates are positioned to overlie each other; and
solder joining the pads on the second and third substrates bonding the first and second substrates to the third substrate.

2. The three dimensional stack of active MEMS devices of claim 1, wherein the substrates further comprise electrical connections from the MEMS device to the pads, and wherein the pads are electrically conducting whereby the pads provide electrical connections to the MEMS devices.

3. The three dimensional stack of active MEMS devices of claim 2, further comprising an underfill material extending between the mounting surfaces of the second and third substrates along at least a portion of a periphery of an adjacent portion those mounting surfaces.

4. The three dimensional stack of active MEMS devices of claim 3, wherein the third substrate further comprises:
a connection section that extends from the second substrate,
a plurality of connection pads on the connection section, and
electrical connections between pads on the third substrate that are joined by solder to pads on the second substrate Whereby connection pads on the third substrate are electrically connected to pads on the second substrate.

5. The three dimensional stack of active MEMS devices of claim 4, wherein the third substrate further comprises a mounting surface that is bonded to an interconnect board.

6. The three dimensional stack of active MEMS devices of claim 5, wherein the interconnect board is made of a material selected from glass and polyimide.

7. The three dimensional stack of active MEMS devices of claim 6, further comprising:
a case having an interior in which the substrates are mounted, the case having an opening adjacent to the MEMS devices and the opening covered by an encapsulation; and
MEMS devices active to extend and retract sensors through the encapsulation.

8. The three dimensional stack of active MEMS devices of claim 7, wherein the encapsulation is a composite of nylon mesh and silicon gel.

9. The three dimensional stack of active MEMS devices of claim 7, wherein one or more substrates has a plurality of active MEMS devices.

10. A method of assembling a three dimensional stack of active MEMS components, the method comprising:

providing a first substrate, the first substrate having:
- a mounting surface,
- an active MEMS device on the mounting surface,
- a plurality of pads formed on the mounting surface, and
- a back surface facing away from the mounting surface;

providing a second substrate, the second substrate having:
- a mounting surface,
- an active MEMS device on the mounting surface,
- a plurality of pads formed on the mounting surface, and
- a back surface facing away from the mounting surface;

bonding the back surface of the second substrate to the back surface of the first substrate so that the active MEMs device on the first substrate is adjacent to the active MEMs device on the second substrate;

providing a third substrate, the third substrate having:
- a mounting surface,
- an active MEMS device on the mounting surface,
- a plurality of pads formed on the mounting surface, the pads and a back surface facing away from the mounting surface;

applying solder to the pads formed on the surface of the third substrate;

positioning the first and second substrates adjacent to and separated from the third substrate with the mounting surface of the second substrate facing the mounting surface of the, third substrate so that the pads on the second and third substrates are positioned to overlie each other and the solder on the third substrate contacts the pads on the second substrate; and bonding the first and second substrates to the third substrate by solder connections.

11. The method of claim 10, further comprising applying an underfill material to extend between the mounting surfaces of the second and third substrates along at least a portion of a periphery of an adjacent portion those mounting surfaces.

12. The method of claim 11 further comprising mounting the third substrate to an interconnect board.

13. The method of claim 12, further comprising:
providing a case having an interior, and
mounting the three dimension stack of active MEMS components to the case and at least partially within the interior.

* * * * *